US010138212B2

United States Patent
Ali et al.

(10) Patent No.: US 10,138,212 B2
(45) Date of Patent: Nov. 27, 2018

(54) AMINOQUINAZOLINE COMPOUNDS AS $A_{2A}$ ANTAGONIST

(71) Applicant: Merck Sharp & Dohme Corp., Rahway, NJ (US)

(72) Inventors: Amjad Ali, Freehold, NJ (US); Rongze Kuang, Green Brook, NJ (US); Yeon-Hee Lim, Piscataway, NJ (US); Michael Man-Chu Lo, Bedminister, NJ (US); Pauline C. Ting, New Providence, NJ (US); Purakkattle Biju, Piscataway, NJ (US); Manuel de Lera Ruiz, Perkasie, PA (US); Sylvia J. Degrado, Scotch Plains, NJ (US); Alexander L. Tung, Bensalem, PA (US); Timothy J. Henderson, Natick, MA (US); Liwu Hong, East Brunswick, NJ (US); Jae-Hun Kim, Scotch Plains, NJ (US); Dong Won-Shik Kim, Rockville, MD (US); Joe Lee, Rahway, NJ (US); Jie Wu, Scotch Plains, NJ (US); Heping Wu, Edison, NJ (US); Yushi Xiao, Rahway, NJ (US); Tao Yu, Edison, NJ (US); Gang Zhou, Bridgewater, NJ (US); Xiaohong Zhu, Edison, NJ (US); Kevin D. McCormick, Basking Ridge, NJ (US); Jayaram R. Tagat, Westfield, NJ (US); Dong Xiao, Warren, NJ (US); Tanweer Khan, Bridgewater, NJ (US); Jianhua Cao, Edison, NJ (US); Michael Berlin, Rahway, NJ (US); Yonglian Zhang, Metuchen, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/549,242

(22) PCT Filed: Feb. 1, 2016

(86) PCT No.: PCT/US2016/015881
§ 371 (c)(1),
(2) Date: Aug. 7, 2017

(87) PCT Pub. No.: WO2016/126570
PCT Pub. Date: Aug. 11, 2016

(65) Prior Publication Data
US 2018/0037554 A1 Feb. 8, 2018

Related U.S. Application Data

(60) Provisional application No. 62/112,747, filed on Feb. 6, 2015.

(51) Int. Cl.
C07D 239/84 (2006.01)
C07D 403/12 (2006.01)
(Continued)

(52) U.S. Cl.
CPC .......... *C07D 239/84* (2013.01); *A61K 31/517* (2013.01); *A61P 25/14* (2018.01);
(Continued)

(58) Field of Classification Search
CPC .. C07D 239/84; C07D 401/12; C07D 471/04; C07D 417/12; C07D 405/12;
(Continued)

(56) References Cited

U.S. PATENT DOCUMENTS

| 5,565,460 A | 10/1996 | Suzuki et al. |
| 6,630,475 B2 | 10/2003 | Neustadt et al. |

(Continued)

FOREIGN PATENT DOCUMENTS

| WO | WO9501356 | 1/1995 |
| WO | WO9705138 | 7/1996 |

(Continued)

OTHER PUBLICATIONS

De Lera Ruiz, M., "Adenosine A2A receptor as a drug discovery target." Journal of medicinal chemistry 57.9 (2013): 3623-3650.*
Berge, S.M., et al.,, "Pharmaceutical Salts", J. Pharm. Sci, 1977, pp. 1-19, vol. 66, No. 1.
Bingham, A.L., et al.,, "Over One Hundred Solvates of sulfathiazole", Chem. Commun., 2001, pp. 603-604.
Caira, M.R., et al.,, "Preparation and Crystal Characterization of a Polymorph,a Monohydrate, and an Ethyl Acetate Solvate of the Antifungal Fluconazole", J. Pharmaceutical Sci., 2004, pp. 601-611, vol. 93, No. 3.
Gould, Salt selection for basic drugs, International J. of Pharmaceutics, 1986, 201-217, 33.

(Continued)

*Primary Examiner* — John M Mauro
(74) *Attorney, Agent, or Firm* — H. Eric Fischer; John C. Todaro

(57) ABSTRACT

The present invention is directed to compounds of generic formula I: or pharmaceutically acceptable salts thereof that are believed to be useful as an A2A-receptor antagonist.

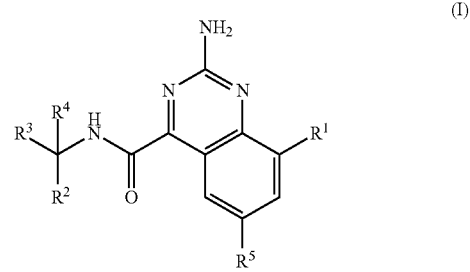

18 Claims, No Drawings

(51) Int. Cl.
  *C07D 401/14* (2006.01)
  *C07D 405/14* (2006.01)
  *C07D 413/14* (2006.01)
  *C07D 401/12* (2006.01)
  *C07D 405/12* (2006.01)
  *C07D 413/12* (2006.01)
  *C07D 417/12* (2006.01)
  *C07D 417/14* (2006.01)
  *C07D 471/04* (2006.01)
  *A61P 25/14* (2006.01)
  *A61K 31/517* (2006.01)

(52) U.S. Cl.
  CPC ......... *C07D 401/12* (2013.01); *C07D 401/14* (2013.01); *C07D 403/12* (2013.01); *C07D 405/12* (2013.01); *C07D 405/14* (2013.01); *C07D 413/12* (2013.01); *C07D 413/14* (2013.01); *C07D 417/12* (2013.01); *C07D 417/14* (2013.01); *C07D 471/04* (2013.01)

(58) Field of Classification Search
  CPC .. C07D 403/12; C07D 413/12; C07D 413/14; C07D 401/14; C07D 417/14
  See application file for complete search history.

(56) References Cited

U.S. PATENT DOCUMENTS

| 2010/0056506 A1 | 3/2010 | Huang et al. |
| 2010/0069383 A1 | 3/2010 | Anderson et al. |
| 2010/0234324 A1 | 9/2010 | Eggenweiler et al. |

FOREIGN PATENT DOCUMENTS

| WO | WO199852568 | 11/1998 |
| WO | WO02055083 | 7/2002 |
| WO | WO2009010139 | 1/2009 |
| WO | WO2010066324 | 6/2010 |
| WO | WO2011060873 | 3/2011 |
| WO | WO2012041435 | 4/2012 |
| WO | WO2014105664 | 7/2014 |
| WO | WO2014105666 | 7/2014 |

OTHER PUBLICATIONS

Stahl et al., Aminoquinazoline Compounds as A2A Antagonist, Handbook of Pharmaceutical Salts Properties, Selection, and Use, 2002, 330-331.

Van Tonder et al., Preparation and Physicochemical Characterization of 5 Niclosamide Solvates and 1 Hemisolvate and 1 Hemisolvate, AAPS PharmSciTech, 2004, Article 12, 5(1).

* cited by examiner

AMINOQUINAZOLINE COMPOUNDS AS $A_{2A}$ ANTAGONIST

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an anti-aggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and nonxanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in PCT International Application Publication Nos. WO 95/01356; U.S. Pat. No. 5,565,460; WO 97/05138; and WO 98/52568. See also WO2009/010139, WO2012/041435, WO2011/060873, and WO2010/066324.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the postsynaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

Formula PI

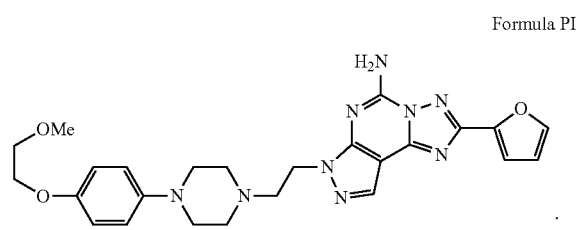 [SMILES: COCCOc1ccc(N2CCN(CCn3ncc4c3nc(N)n3nc(-c5ccco5)nc43)CC2)cc1]

In the '475 patent example Schemes 1 to 5, along with preparative Schemes 1 to 4, show general methods of preparing compounds of Formula PI. The '475 patent describes also that the compound of Formula I can be prepared as a pharmaceutically acceptable salt which may be useful for treating Parkinson's disease.

The use of $A_{2A}$ receptor antagonists in the potential treatment of central nervous system diseases, in particular Parkinson's disease, and to pharmaceutical compositions comprising said compounds has elevated the need for potent, moderately lipophilic, brain penetrant inhibitors of the $A_{2A}$ receptor. Such compounds would provide an expansion of the arsenal of compounds which are believed to have value in the treatment of central nervous system disorders, in particular treating or managing the progression of such diseases, for example, but not limited to, Parkinson's disease.

SUMMARY OF THE INVENTION

The present invention is directed to compounds of generic formula (I) below or pharmaceutically acceptable salts thereof that are believed to be useful as an $A_{2A}$-receptor antagonist.

The invention is further directed to methods of treating a patient (preferably a human) for diseases or disorders in which the $A_{2A}$-receptor is involved. The invention further involves use of the compounds as an $A_{2A}$-receptor antagonist and/or inhibitor for the preparation of a medicament for the treatment and/or prevention of diseases associated with inhibiting the receptor, which includes central nervous system disorders such as Parkinson's disease. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one aspect, the invention is directed to compounds of general formula I:

![Formula I structure: quinazoline with NH2 at 2-position, R1 at 8-position, R5 at 6-position, and C(=O)NH-CR4(R2)(R3) at 4-position]

I or a pharmaceutically acceptable salt thereof, wherein:

R represents hydrogen or —$C_{1-6}$alkyl;

$R^1$ is selected from the group consisting of —$C_{1-6}$alkyl, —$OC_{1-6}$alkyl, halogen, —$C_{1-4}$ haloalkyl, —$OC_{1-4}$haloalkyl, CN, —$SC_{1-6}$alkyl, —$SO_2C_{1-6}$alkyl, and —$(CH_2)_nC_{4-10}$ heteroaryl;

$R^2$ and $R^3$ when present are independently selected from the group consisting of hydrogen, deuterated hydrogen (D), $C_{3-10}$cycloalkyl, and $C_{1-6}$ alkyl, said alkyl optionally substituted with 1 to 3 groups of $R^b$; or $R^2$ and $R^3$ can combine to form a 3 to 6 membered cycloalkyl ring;

$R^4$ when present represents —$(CH_2)_nC_{6-10}$ aryl, or —$(CH_2)_nC_{4-10}$ heterocycle, said aryl and heterocycle optionally substituted with 1 to 3 groups of $R^a$; or $R^2$, $R^3$ and $R^4$ can combine to form a $C_{4-10}$ heterocyclic group, said heterocyclic group optionally substituted with 1 to 3 groups of $R^a$;

R5 represents hydrogen or halogen;

$R^a$ is selected from the group consisting of —CN, halogen, —$C_{1-4}$haloalkyl, —$OC_{1-4}$haloalkyl, —$C_{1-6}$alkyl, —$(CH_2)_nOR$, —$(CH_2)_nC_{6-10}$ aryl, —$(CH_2)_nC_{4-10}$ heterocycle, —$(CH_2)_nO(CH_2)_n$ $C_{3-6}$cycloalkyl, $C_{3-6}$cycloalkyl, $C(C_{3-6}$cycloalkyl)OR, —$(CH_2)_nO(CH_2)_nC_{6-10}$ aryl, —$(CH_2)_nO(CH_2)_nC_{4-10}$ heterocycle, —$(CH_2)_nSC_{6-10}$ aryl, —$(CH_2)_nSC_{4-10}$ heterocycle, =O, C(O)OR, said alkyl, cycloalkyl, aryl and heterocycle optionally substituted with 1 to 3 groups of $R^b$;

$R^b$ is selected from the group consisting of —$C_{1-6}$alkyl, —$C_{1-6}$alkylOR, OR, $O(CH_2)_{1-2}OR$, —$C_{1-4}$haloalkyl, halogen, CN, —$C_{6-10}$ aryl, —$C_{4-10}$ heterocycle, $C(CH_3)_2O(CH_2)_{1-2}OR$, said alkyl, aryl and heterocycle optionally substituted with 1 to 3 groups of $R^c$;

$R^c$ is selected from the group consisting of —$C_{1-6}$alkyl, halogen, —$C_{1-6}$alkylOR, $O(CH_2)_{1-2}OR$ OR, and n represents 0-4.

An embodiment of the invention of formula I is realized when hydrogen can be deuterated.

An embodiment of the invention of formula I is realized when $R^1$ is selected from the group consisting of —$OC_{1-6}$alkyl, —$C_{1-4}$ haloalkyl, —$OC_{1-4}$haloalkyl, and halogen. A subembodiment of this aspect of the invention is realized when $R^1$ is —$OC_{1-6}$alkyl. A further subembodiment of this aspect of the invention is realized when $R^1$ is —$OCH_3$. Still another subembodiment of this aspect of the invention is realized when $R^1$ is $CF_3$ or $OCF_3$. Yet another subembodiment of this aspect of the invention is realized when $R^1$ is halogen.

Another embodiment of the invention of formula I is realized when $R^2$ and $R^3$ are both hydrogen.

Another embodiment of the invention of formula I is realized when $R^2$ and $R^3$ are both $C_{1-6}$ alkyl.

Another embodiment of the invention of formula I is realized when one of $R^2$ and $R^3$ is hydrogen and the other is optionally substituted $C_{1-6}$alkyl.

Another embodiment of the invention of formula I is realized when $R^2$ and $R^3$ are both deuterated hydrogen.

Another embodiment of the invention of formula I is realized when $R^2$ and $R^3$ are both absent and $R^4$ is present.

Another embodiment of the invention of formula I is realized when $R^4$ is absent, one of $R^2$ and $R^3$ is $C_{1-6}$alkyl and the other $C_{3-10}$cycloalkyl. An aspect of this embodiment of the invention is realized when the cycloalkyl is adamantly or norbornanyl.

Still another embodiment of the invention of formula I is realized when $R^4$ is present, and $R^2$ and $R^3$ combine to form a 3 to 6 membered cycloalkyl ring selected from the group consisting of cyclopropyl, cyclobutyl, cyclopentyl and cyclohexyl. A subembodiment of this aspect of the invention is realized when $R^2$ and $R^3$ combine to form cyclopropyl.

Another embodiment of the invention of formula I is realized when $R^2$ and $R^3$ are present and $R^4$ is —$(CH_2)_nC_{6-10}$ aryl, said aryl group optionally substituted with 1 to 3 groups of $R^a$. A subembodiment of this aspect of the invention is realized when $R^4$ is substituted —$(CH_2)_nC_{6-10}$ aryl. Still another subembodiment of this aspect of the invention is realized when the aryl of $R^4$ is selected from the group consisting of unsubstituted or substituted phenyl and napthyl. A subembodiment of this aspect of the invention is realized when the aryl of $R^4$ is substituted phenyl. A subembodiment of this aspect of the invention is realized when the aryl of $R^4$ is substituted napthyl.

Another embodiment of the invention of formula I is realized when $R^2$ and $R^3$ are present and $R^4$ is —$(CH_2)_nC_{4-10}$ heterocycle, said heterocycle group optionally substituted with 1 to 3 groups of $R^a$. A subembodiment of this aspect of the invention is realized when $R^4$ is substituted —$(CH_2)_nC_{4-10}$ heterocycle. Still another subembodiment of this aspect of the invention is realized when the heterocycle of $R^4$ is selected from the group consisting of unsubstituted or substituted pyridyl, quinolyl, pyridinone, oxazolyl, pyrimidinyl, benzodioxolyl, imidazopyridyl, thiazolyl, isoxazolyl, dihydrobenzoxazinyl adamantly, piperidyl, and norbornanyl. Still another subembodiment of this aspect of the invention is realized when the heterocycle of $R^4$ is selected from the group consisting of substituted pyridyl, quinolyl, pyridinone, oxazolyl, pyrimidinyl, benzodioxolyl, imidazopyridyl, thiazolyl, isoxazolyl, dihydrobenzoxazinyl adamantly, piperidyl, and norbornanyl. Yet another aspect of the invention is realized when the heterocycle of $R^4$ is selected from the group consisting of unsubstituted or substituted pyridyl, quinolyl, and pyrimidinyl. Still another aspect of the invention is realized when the heterocycle of $R^4$ is unsubstituted or substituted pyridyl. Still another aspect of the invention is realized when the heterocycle of $R^4$ is unsubstituted or substituted quinolyl. Yet another aspect of the invention is realized when the heterocycle of $R^4$ is unsubstituted or substituted pyrimidinyl. Yet another aspect of the invention is realized when the heterocycle of $R^4$ is unsubstituted or substituted pyridinone. Yet another aspect of the invention is realized when the heterocycle of $R^4$ is unsubstituted or substituted oxazolyl. Yet another aspect of the invention is realized when the heterocycle of $R^4$ is unsubstituted or substituted benzodioxolyl. Yet another aspect of the invention is realized when the heterocycle of $R^4$ is unsubstituted or substituted imidazopyridyl. Yet another aspect of the invention is realized when the heterocycle of $R^4$ is unsubstituted or substituted thiazolyl. Yet another aspect of the invention is realized when the heterocycle of $R^4$ is unsubstituted or substituted isoxazolyl. Yet another aspect of the invention is realized when the heterocycle of $R^4$ is unsubstituted or substituted dihydrobenzoxazinyl. Yet another aspect of the invention is realized when the heterocycle of $R^4$ is unsubstituted or substituted adamantly. Yet another aspect of the invention is realized when the heterocycle of $R^4$ is unsubstituted or substituted piperidyl. Yet another aspect of the invention is realized when the heterocycle of $R^4$ is unsubstituted or substituted norbornanyl.

Yet another embodiment of the invention of formula I is realized when $R^2$, $R^3$ and $R^4$ combine to form a $C_{4-10}$ heterocyclic group selected from the group consisting of indanyl, dihydrocyclopentapyridinyl, tetralinyl, and tetrahydroquinolinyl, said groups optionally substituted with 1 to 3 groups of $R^a$.

Another embodiment of the invention of formula I is realized when $R^5$ is hydrogen. Still another embodiment of the invention of formula I is realized when $R^5$ is halogen selected from the group consisting of chlorine, fluorine, bromine and iodine. Yet another aspect of the invention is realized when $R^5$ is chlorine.

Yet another embodiment of the invention of formula I is realized when $R^a$ is selected from the group consisting of halogen, —$C_{1-4}$haloalkyl, —$C_{1-6}$alkyl, —$(CH_2)_nOR$, —$(CH_2)_nC_{6-10}$ aryl, —$(CH_2)_nC_{4-10}$ heterocycle, —$(CH_2)O(CH_2)_nC_{6-10}$ aryl, —$(CH_2)O(CH_2)_nC_{4-10}$ heterocycle, $C_{3-6}$ cycloalkyl, —O—, C(O)OR, said alkyl, aryl and heterocycle optionally substituted with 1 to 3 groups of $R^b$. In some embodiments of this invention —$(CH_2)_nC_{6-10}$ aryl and —$(CH_2)_nC_{4-10}$ heterocycle are —$(CD_2)_nC_{6-10}$ aryl, —$(CD_2)_nC_{4-10}$ heterocycle Another embodiment the invention of formula I is realized when $R^a$ is selected from the group consisting of —$C(CH_3)_2OH$, $OCH_3$, $CF_3$, —$OCH(CH_3)_2$, methyl, ethyl, propyl, butyl, —$CH(CH_3)_2$, —$(CH_3)_2(CF_3)OH$, $CH_2OCH_2C(CH_3)_2$, —$C(cyclobutyl)OH$, $CH_2OH$, fluorine, chlorine, bromine, iodine, cyclobutyl, cyclopropyl, $(CH_2)_n$phenyl, $(CH_2)_n$pyridyl, $(CH_2)_n$piperidyl, $(CH_2)_n$piperizinyl, oxo, $(CH_2)_n$pyrazolyl, $(CH_2)_n$pyrimidinyl, $(CH_2)_n$thiazolyl, $(CH_2)_n$oxazolyl, $C(O)OCH_3$, $(CH_2)_n$morpholinyl, $(CH_2)_n$—O-phenyl, $(CH_2)_n$—S-phenyl, $(CH_2)_n$—O-pyridyl, $(CH_2)_n$—S-pyridyl, $(CH_2)_n$—S-benzimidazolyl, $CH_2$—O—$CH_2$-cyclopentyl, $(CH_2)_n$—O-tetrahydrofuranyl, $(CD_2)_n$phenyl, and $(CD_2)_n$pyridyl, said methyl, ethyl, propyl, butyl, phenyl, pyridyl, piperidyl, piperizinyl, pyrazolyl, pyrimidinyl, thiazolyl, oxazolyl, morpholinyl, and benzimidazolyl optionally substituted with 1 to 3 groups of $R^b$. A subembodiment of this aspect of the invention is realized when $R^a$ is selected from the group consisting of —$C(CH_3)_2OH$, $OCH_3$, $CF_3$, —$OCH(CH_3)_2$, methyl, ethyl, propyl, butyl, —$CH(CH_3)_2$, —$(CH_3)_2(CF_3)OH$, $CH_2OCH_2C(CH_3)_2$, $CH_2OH$, fluorine, $(CH_2)_n$phenyl, $(CH_2)_n$pyridyl, $(CD_2)_n$phenyl, and $(CD_2)_n$pyridyl, said methyl, ethyl, propyl, butyl, phenyl and pyridyl optionally substituted with 1 to 3 groups of $R^b$.

Still another embodiment of the invention of formula I is realized when $R^b$ is selected from —$C_{1-6}$alkyl, OR, —$C_{1-4}$haloalkyl, halogen, CN, $O(CH_2)_nOCH_3$, phenyl, $CH(CH_3)_2$, $OCH(CH_3)_2$, $C(CH_3)_2O(CH_2)_nOCH_3$, morpholinyl, oxazolyl, said alkyl, phenyl, morpholinyl, and oxazolyl optionally substituted with 1 to 3 groups of $R^c$.

Another embodiment of the invention of formula I is represented by structural formula II:

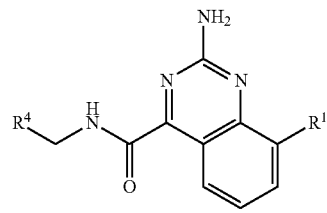

or a pharmaceutically acceptable salt thereof, wherein $R^4$ and $R^1$ are as originally described.

A subembodiment of the invention of formula II is realized when $R^4$ is —$(CH_2)_nC_{6-10}$ aryl optionally substituted with 1 to 3 groups of $R^a$. A subembodiment of this aspect of the invention is realized when the optionally substituted aryl is phenyl.

Another subembodiment of the invention of formula II is realized when $R^4$ is —$(CH_2)_nC_{4-10}$ heterocycle, said heterocycle optionally substituted with 1 to 3 groups of $R^a$. A subembodiment of this aspect of the invention is realized when the heterocycle is selected from the group consisting of pyridyl, pyridinone, quinolyl, oxazolyl, pyrimidinyl, benzodioxolyl, imidazopyridinyl, thiazolyl, isoxazolyl, dihydrobenzoxazinyl, adamantly, piperidyl, and norboranyl, said groups optionally substituted with 1 to 3 groups of $R^a$. A further subembodiment of the invention of formula II is realized when $R^4$ is substituted with 1 group of $R^a$. A further subembodiment of this aspect of the invention is realized when $R^4$ is substituted with 1 to 2 groups of $R^a$.

Another subembodiment of the invention of formula II is realized when $R^4$ is unsubstituted or substituted phenyl.

Another subembodiment of the invention of formula II is realized when $R^4$ is unsubstituted or substituted pyridyl. An aspect of this subembodiment of the invention of formula II is realized when $R^4$ pyridyl is represented by structural formula $R^{4a}$, $R^{4b}$ or $R^{4c}$:

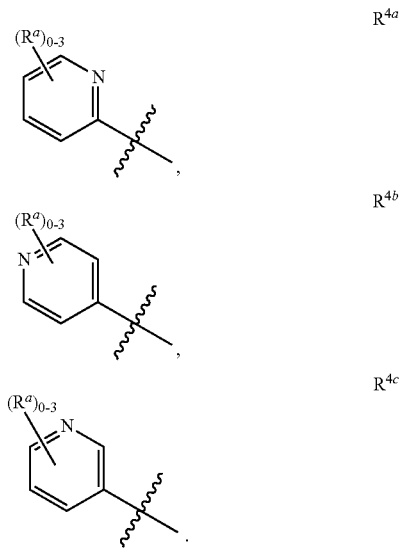

Another aspect of the subembodiment of the invention of formula II is realized when $R^4$ pyridyl is $R^{4a}$. Another aspect of the subembodiment of the invention of formula II is realized when $R^4$ pyridyl is $R^{4b}$. Another aspect of the subembodiment of the invention of formula II is realized when $R^4$ pyridyl is $R^{4c}$. Another aspect of the subembodiment of the invention of formula II is realized when $R^a$ in structural formula $R^{4a}$, $R^{4b}$ or $R^{4c}$ is 1. Still another aspect of the subembodiment of the invention of formula II is realized when $R^a$ in structural formula $R^{4a}$, $R^{4b}$ or $R^{4c}$ is 1 to 2.

Another subembodiment of the invention of formula II is realized when $R^4$ is unsubstituted or substituted pyridinone.

Another subembodiment of the invention of formula II is realized when $R^4$ is unsubstituted or substituted quinolyl. An aspect of this subembodiment of the invention of formula II is realized when $R^4$ is represented by structural formula $R^{4d}$, $R^{4e}$ or $R^{4f}$:

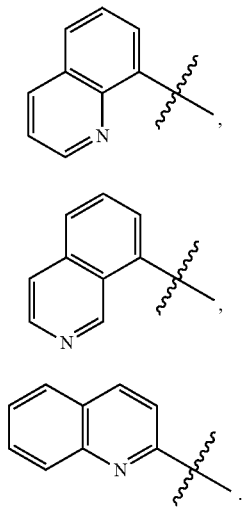

Another aspect of this subembodiment of the invention of formula II is realized when $R^4$ quinolyl is $R^{4d}$. Another aspect of this subembodiment of the invention of formula II is realized when $R^4$ quinolyl is $R^{4e}$. Another aspect of this subembodiment of the invention of formula II is realized when $R^4$ pyridyl is $R^{4f}$.

Another subembodiment of this aspect of the invention of formula II is realized when $R^4$ is unsubstituted or substituted oxazolyl.

Another subembodiment of this aspect of the invention of formula II is realized when $R^4$ is unsubstituted or substituted pyrimidinyl.

Another subembodiment of this aspect of the invention of formula II is realized when $R^4$ is unsubstituted or substituted benzodioxolyl.

Another subembodiment of this aspect of the invention of formula II is realized when $R^4$ is unsubstituted or substituted imidazopyridinyl.

Another subembodiment of this aspect of the invention of formula II is realized when $R^4$ is unsubstituted or substituted thiazolyl.

Another subembodiment of this aspect of the invention of formula II is realized when $R^4$ is unsubstituted or substituted isoxazolyl.

Another subembodiment of this aspect of the invention of formula II is realized when $R^4$ is unsubstituted or substituted dihydrobenzoxazinyl.

Another subembodiment of this aspect of the invention of formula II is realized when $R^4$ is unsubstituted or substituted piperidyl.

Another subembodiment of the invention of formula II is realized when $R^1$ is selected from the group consisting of $OC_{1-6}$alkyl, —$C_{1-4}$ haloalkyl, —$OC_{1-4}$haloalkyl, and halogen. A further aspect of this subembodiment of the invention of formula II is realized when $R^1$ is selected from the group consisting of $OCH_3$, fluorine, chlorine, bromine, iodine, CN, $CF_3$, $SCH_3$, pyrimidinyl, and oxazolyl. Still another aspect of this subembodiment of formula II is realized when $R^1$ is $OCH_3$. Yet another aspect of this subembodiment is realized when $R^1$ is fluorine.

Still another subembodiment of the invention of formula II is realized when $R^4$ is selected from the group consisting of phenyl, pyridyl, pyridinone, quinolyl, oxazolyl, imidazopyridinyl, thiazolyl, isoxazolyl, and piperidyl, said groups substituted with 1 to 3 groups of $R^a$ selected from the group consisting of selected from the group consisting of halogen, —$C_{1-4}$haloalkyl, —$C_{1-6}$alkyl, —$(CH_2)_nOR$, —$(CH_2)_nC_{6-10}$ aryl, —$(CH_2)_nC_{4-10}$ heterocycle, —$(CH_2)O(CH_2)_nC_{6-10}$ aryl, —$(CH_2)O(CH_2)_nC_{4-10}$ heterocycle, $C_{3-6}$cycloalkyl, —O—, C(O)OR, said alkyl, aryl and heterocycle optionally substituted with 1 to 3 groups of $R^b$. A subembodiment of this aspect of the invention of formula II is realized when $R^a$ is selected from the group consisting of —$C(CH_3)_2OH$, $OCH_3$, $CF_3$, —$OCH(CH_3)_2$, methyl, ethyl, propyl, butyl, —$CH(CH_3)_2$, —$(CH_3)_2(CF_3)OH$, $CH_2OCH_2C(CH_3)_2$, —$C(cyclobutyl)OH$, $CH_2OH$, fluorine, chlorine, bromine, iodine, cyclobutyl, cyclopropyl, $(CH_2)_n$phenyl, $(CH_2)_n$pyridyl, $(CH_2)_n$piperidyl, $(CH_2)_n$piperizinyl, oxo, $(CH_2)_n$pyrazolyl, $(CH_2)_n$pyrimidinyl, $(CH_2)_n$thiazolyl, $(CH_2)_n$oxazolyl, $C(O)OCH_3$, $(CH_2)_n$morpholinyl, $(CH_2)_n$—O-phenyl, $(CH_2)_n$—S-phenyl, $(CH_2)_n$—O-pyridyl, $(CH_2)_n$—S-pyridyl, $(CH_2)_n$—S-benzimidazolyl, $CH_2$—O—$CH_2$-cyclopentyl, $(CH_2)_n$—O-tetrahydrofuranyl, $(CD_2)_n$phenyl, and $(CD_2)_n$pyridyl, said methyl, ethyl, propyl, butyl, phenyl, pyridyl, piperidyl, piperizinyl, pyrazolyl, pyrimidinyl, thiazolyl, oxazolyl, morpholinyl, and benzimidazolyl optionally substituted with 1 to 3 groups of $R^b$.

An embodiment of the invention of formula II is realized when $R^4$ is phenyl, quinolyl, or pyridyl, said groups substituted with 1 to 3 groups selected from —$C(CH_3)_2OH$, $OCH_3$, $CF_3$, —$OCH(CH_3)_2$, methyl, ethyl, propyl, butyl, —$CH(CH_3)_2$, —$(CH_3)_2(CF_3)OH$, $CH_2OCH_2C(CH_3)_2$, —$C(cyclobutyl)OH$, $CH_2OH$, fluorine, chlorine, bromine, iodine, cyclobutyl, cyclopropyl, $(CH_2)_n$phenyl, $(CH_2)_n$pyridyl, $(CH_2)_n$piperidyl, $(CH_2)_n$piperizinyl, oxo, $(CH_2)_n$pyrazolyl, $(CH_2)_n$pyrimidinyl, $(CH_2)_n$thiazolyl, $(CH_2)_n$oxazolyl, $C(O)OCH_3$, $(CH_2)_n$morpholinyl, $(CH_2)_n$—O-phenyl, $(CH_2)_n$—S-phenyl, $(CH_2)_n$—O-pyridyl, $(CH_2)_n$—S-pyridyl, $(CH_2)_n$—S-benzimidazolyl, $CH_2$—O—$CH_2$-cyclopentyl, $(CH_2)_n$—O-tetrahydrofuranyl, $(CD_2)_n$phenyl, and $(CD_2)_n$pyridyl, said methyl, ethyl, propyl, butyl, phenyl, pyridyl, piperidyl, piperizinyl, pyrazolyl, pyrimidinyl, thiazolyl, oxazolyl, morpholinyl, and benzimidazolyl optionally substituted with 1 to 3 groups of $R^b$ and $R^1$ is selected from the group consisting of $OC_{1-6}$alkyl, —$C_{1-4}$ haloalkyl, —$OC_{1-4}$haloalkyl, and halogen.

A subembodiment of this aspect of the invention of formula II is realized when $R^4$ is phenyl substituted with 1 to 3 groups of $R^a$ selected from the group consisting of —$C(CH_3)_2OH$, $OCH_3$, $CF_3$, —$OCH(CH_3)_2$, methyl, ethyl, propyl, butyl, —$CH(CH_3)_2$, —$(CH_3)_2(CF_3)OH$, $CH_2OCH_2C(CH_3)_2$, $CH_2OH$, fluorine, $(CH_2)_n$phenyl, $(CH_2)_n$pyridyl, $(CD_2)_n$phenyl, and $(CD_2)_n$pyridyl, said methyl, ethyl, propyl, butyl, phenyl and pyridyl optionally substituted with 1 to 3 groups of $R^b$ and $R^1$ is selected from the group consisting of $OC_{1-6}$alkyl, —$C_{1-4}$ haloalkyl, —$OC_{1-4}$haloalkyl, and halogen and $R^b$ is selected from —C$_{1-6}$alkyl, OR, —C$_{1-4}$haloalkyl, halogen, CN, O(CH$_2$)$_n$OCH$_3$, phenyl, CH(CH$_3$)$_2$, OCH(CH$_3$)$_2$, C(CH$_3$)$_2$O(CH$_2$)$_n$OCH$_3$, morpholinyl, oxazolyl, said alkyl, phenyl, morpholinyl, and oxazolyl optionally substituted with 1 to 3 groups of R$^c$. A further subembodiment of this aspect of the invention is realized when R$^1$ is OCH$_3$. Another further subembodiment of this aspect of the invention is realized when R$^1$ is fluorine.

Another subembodiment of this aspect of the invention of formula II is realized when R$^4$ is pyridyl substituted with 1 to 3 groups of R$^a$ selected from the group consisting of —C(CH$_3$)$_2$OH, OCH$_3$, CF$_3$, —OCH(CH$_3$)$_2$, methyl, ethyl, propyl, butyl, —CH(CH$_3$)$_2$, —(CH$_3$)$_2$(CF$_3$)OH, CH$_2$OCH$_2$C(CH$_3$)$_2$, CH$_2$OH, fluorine, (CH$_2$)$_n$phenyl, (CH$_2$)$_n$pyridyl, (CD$_2$)$_n$phenyl, and (CD$_2$)$_n$pyridyl, said methyl, ethyl, propyl, butyl, phenyl and pyridyl optionally substituted with 1 to 3 groups of R$^b$ and R$^1$ is selected from the group consisting of OC$_{1-6}$ alkyl, —C$_{1-4}$ haloalkyl, —OC$_{1-4}$haloalkyl, and halogen and R$^b$ is selected from —C$_{1-6}$alkyl, OR, —C$_{1-4}$haloalkyl, halogen, CN, O(CH$_2$)$_n$OCH$_3$, phenyl, CH(CH$_3$)$_2$, OCH(CH$_3$)$_2$, C(CH$_3$)$_2$O(CH$_2$)$_n$OCH$_3$, morpholinyl, oxazolyl, said alkyl, phenyl, morpholinyl, and oxazolyl optionally substituted with 1 to 3 groups of R$^c$. A further subembodiment of this aspect of the invention is realized when R$^1$ is OCH$_3$. Another further subembodiment of this aspect o the invention is realized when R$^1$ is fluorine.

Another subembodiment of this aspect of the invention of formula II is realized when R$^4$ is quinolyl substituted with 1 to 3 groups of R$^a$ selected from the group consisting of —C(CH$_3$)$_2$OH, OCH$_3$, CF$_3$, —OCH(CH$_3$)$_2$, methyl, ethyl, propyl, butyl, —CH(CH$_3$)$_2$, —(CH$_3$)$_2$(CF$_3$)OH, CH$_2$OCH$_2$C(CH$_3$)$_2$, CH$_2$OH, fluorine, (CH$_2$)$_n$phenyl, (CH$_2$)$_n$pyridyl, (CD$_2$)$_n$phenyl, and (CD$_2$)$_n$pyridyl, said methyl, ethyl, propyl, butyl, phenyl and pyridyl optionally substituted with 1 to 3 groups of R$^b$ and R$^1$ is selected from the group consisting of OC$_{1-6}$alkyl, —C$_{1-4}$ haloalkyl, —OC$_{1-4}$haloalkyl, and halogen and R$^b$ is selected from —C$_{1-6}$alkyl, OR, —C$_{1-4}$haloalkyl, halogen, CN, O(CH$_2$)$_n$OCH$_3$, phenyl, CH(CH$_3$)$_2$, OCH(CH$_3$)$_2$, C(CH$_3$)$_2$O(CH$_2$)$_n$OCH$_3$, morpholinyl, oxazolyl, said alkyl, phenyl, morpholinyl, and oxazolyl optionally substituted with 1 to 3 groups of R$^c$. A further subembodiment of this aspect of the invention is realized when R$^1$ is OCH$_3$. Another further subembodiment of this aspect of the invention is realized when R$^1$ is fluorine.

Examples of the compounds of this invention include those in Tables IIIa, IIIb, and IV herein.

As used herein, unless otherwise specified, the term "A2a receptor antagonist" (equivalently, A2a antagonist) means a compound exhibiting a potency (EC$_{50}$) of less than about 1 μM when assayed in accordance with the procedure described herein. Preferred compounds exhibit at least 100-fold selectivity for antagonizing the A2a receptor over any other adenosine receptor (e.g., A1, A2b, or A3).

Compounds of the invention and formulations comprising compounds of the invention are believed to be useful in providing potential treatment, management, alleviation or amelioration of conditions or disease states which can be treated, managed, alleviated or ameliorated by specific antagonism of A2a receptors. Conditions for which such therapy may be provided include, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential, or are believed to have the potential, for use in preventing or lessening the effect of drugs that cause movement disorders As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

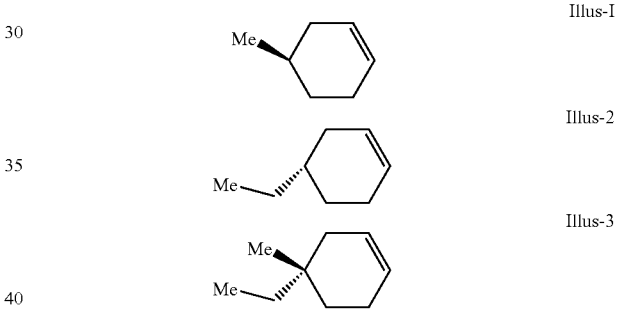

Illus-I

Illus-2

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents (or, where a list of substituents are not specifically enumerated, the default substituents specified in this "Definitions" section for the particular type of substrate which contains variable substituents) can occupy one or more of the bonding positions on the substrate typically occupied by "—H", provided that such substitution does not exceed the normal valency rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated (or default substituents for the specified substrate, for example, hydrogen on an alkyl or aromatic moiety) can be present on the substrate in a bonding position normally occupied by the default substituent, for example, a hydrogen atom, in accordance with the definition of "substituted" presented herein.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C═O)—" or "R'—C(O)—", or by the structural representation:

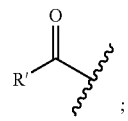

"alkoxy" means a moiety of the structure: alkyl-O— (i.e., the bond to the substrate moiety is through the oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". The term "alkyl" is further defined by "Linear", or "Branched". Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term cycloalkyl means a moiety having a main hydrocarbon chain forming a cyclic aliphatic moiety comprising at least 3 carbon atoms (the minimum number necessary to provide a cyclic moiety) up to the maximum number of specified carbon atoms. Examples of cycloalkyl moieties include, but are not limited to, cyclopropyl, cyclobutyl, cyclopentyl or cyclohexyl. The term cycloalkyl also includes non-aromatic, fused multicyclic ring system comprising up to about 20 carbon atoms which may optionally be substituted as defined herein. Suitable multicyclic cycloalkyls are, for example, but are not limited to: 1-decalin; norbornyl; adamantly; and the like;

Any of the afore-mentioned linear-, branched-, or cycloalkyl moieties which are defined to be "optionally substituted" means that one or more of the carbon atoms in the structure can have one or more of the C—H bonds associated therewith substituted with a substituent selected from the list of substituents called out in the definition of the moiety.

"lower alkyl" means a linear, branched, or cycloalkyl moiety comprising up to about 6 carbon atoms; non-limiting examples of suitable lower alkyl groups include methyl, ethyl, n-propyl, isopropyl, cyclopropyl, n-butyl, t-butyl, cyclobutyl, n-pentyl, isopentyl, neopentyl, cyclopentyl, n-hexyl, cyclohexyl and the like;

"aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); the aryl group can be optionally substituted with one or more independently selected "ring system substituents" (defined below). Non-limiting examples of suitable aryl groups include phenyl

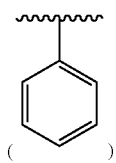

and naphthyl

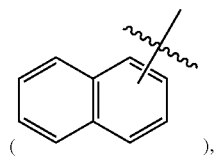

wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"arylalkyl-" means and aryl-$C_{1-6}$-alkyl group (i.e., the moiety is bonded to the substrate through a lower alkyl group) wherein the aryl group is as defined above;

"arylcycloalkyl" means a moiety having an aryl-portion fused to two carbon atoms of a cycloalkyl portion, wherein either portion may be optionally substituted with one or more ring-system substituents, and wherein the aryl portion and the cycloalkyl portion comprises up to 10 carbon atoms in the ring, and in some embodiments the cycloalkyl portion preferably comprises 6 carbon atoms. Examples of arylcycloalkyl moieties include, but are not limited to, tetrahydroanthracene, tetrahydronaphthalene, dihydroindene, and the like. Unless specified otherwise, bonding of an arylcycloalkyl moiety to a substrate may be through any aryl or cycloalkyl ring carbon atom. When the term is used with "spiro", e.g. "arylspirocycloalkyl" it means that the alkyl portion of the moiety contains one carbon in common with a substrate to which it is attached forming a spirocylo structure, for example, the structure:

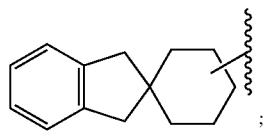

wherein the structure is bonded to a substrate through the cycloalkyl portion with which the arylcycloalkyl moiety forms a spirocyloalkyl structure;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$;

"heterocyclyl", "heterocycle" or "heterocyclic", represents a stable 5- to 7-membered monocyclic or stable 8- to 11-membered bicyclic heterocyclic ring which is either saturated, partially saturated, or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. The nitrogen or sulfur atom of the heterocyclyl can be optionally oxidized to the corresponding N-oxide, S-oxide or S,S-dioxide ($SO_2$). Non-limiting examples of suitable unsaturated monocyclic heterocyclyl rings include piperidyl, pyrrolidinyl, piperazinyl, morpholinyl-

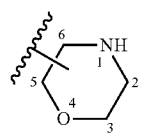

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

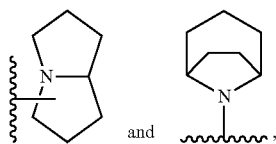

and the like. Other examples of saturated, partially saturated and unsaturated heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyly, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, naphthyridinyl, oxadiazolyl, 2-oxoazepinyl, oxazolyl, 2-oxopiperazinyl, 2-oxopiperdinyl, 2-oxopyrrolidinyl, pyridyl, pyrazinyl, pyrazolidinyl, pyrazolyl, pyrazolopyridinyl, pyridazinyl, pyrimidinyl, pyrrolyl, quinazolinyl, quinolinyl, quinoxalinyl, tetrahydroisoquinolinyl, tetrahydroquinolinyl, thiamorpholinyl, thiamorpholinyl sulfoxide, thiazolyl, thienofuryl, thienothienyl, thienyl, triazolyl, N-oxides and —C=O derivatives thereof.

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: pyridyl-,

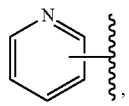

thiopenyl-

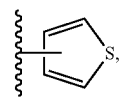

furanyl-,

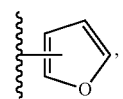

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, and, for example, heteroaryl moieties of the following structure:

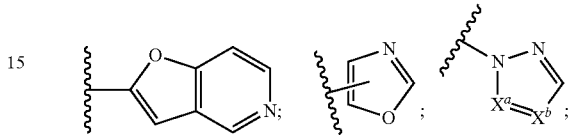

where one of $X^a$ or $X^b$ is —CH= or —N= and the other is —CH=;

and the like (wherein, unless otherwise noted, bonded to the substrate through any available ring atom that results in a stable bonding arrangement);

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

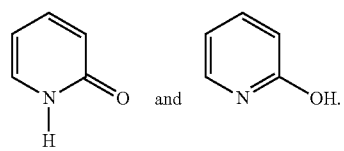 [SMILES: O=c1cccc[nH]1 ; "and" ; Oc1ccccn1]

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, heterocycl, $R^{XY}$, etc.) appears more than once in any moiety or in any compound of the invention, the selection of moieties defining that variable for each occurrence is independent of its definition at every other occurrence unless specified otherwise in the local variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by know means also.

Certain isotopically-labeled compounds of the invention (e.g., those labeled with $^3H$, $^{11}C$ and 14C) are recognized as being particularly useful in compound and/or substrate tissue distribution assays using a variety of known techniques. Tritiated (i.e., $^3H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

In one aspect, as mentioned above, the present invention provides pharmaceutical formulations (pharmaceutical compositions) for use in antagonizing $A_{2A}$ receptors, believed to be useful in treating central nervous system (CNS) disorders, for example, movement disorders associated with Parkinson's disease or the treatment thereof, wherein the compositions comprising at least one compound, or pharmaceutically acceptable salt thereof, of Formula I or Formula II, as defined herein.

As mentioned above, in one aspect the invention provides pharmaceutical formulations (pharmaceutical compositions) suitable for use in blocking adenosine A2a receptors found in the basal ganglia, comprising at least one compound of Formula I or Formula II presented above, or a pharmaceutically acceptable salt thereof, and at least one pharmaceutically acceptable carrier (described below). It will be appreciated that pharmaceutical formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of compounds of the invention, one or more other compounds which also have pharmacological activity, for example, as described herein below.

In some embodiments the formulation preferably comprises one or more compounds of Formula I or Formula II, as defined herein, and at least one pharmaceutically acceptable carrier (described below). It will be appreciated that pharmaceutical formulations of the invention may comprise more than one compound of the invention, for example, the combination of two or three compounds of Formula I or Formula II, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula I. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle and process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for use of the compounds described herein for the potential treatment, management, alleviation or amelioration of conditions or disease states which can be, or are believed to be, treated, managed, alleviated or ameliorated by specific antagonism of adenosine A2a receptors, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential for use in preventing or lessening the effect of drugs that cause movement disorders.

In accordance with the present invention, antagonism of adenosine A2a receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, for example, a compound of Formula I or Formula II, or a salt of either thereof, and at least one pharmaceutically acceptable carrier. It will be appreciated that pharmaceutically formulations of the invention may comprise more than one compound of the invention, or a salt thereof, for example, the combination of two or three compounds of the invention, each present by adding to the formulation the desired amount of the compound or a salt thereof which has been isolated in a pharmaceutically acceptably pure form.

As mentioned above, administration of a compound of the invention to effect antagonism of A2a receptor sites, which is believed to be beneficial in the treatment of central nervous system diseases is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

As mentioned above, administration of a compound of the invention is preferably accomplished by incorporating the compound into a pharmaceutical formulation incorporated into a dosage form, for example, one of the above-described dosage forms comprising an effective amount of at least one compound of the invention (for example, 1, 2 or 3, or 1 or 2, or 1, and usually 1 compound of the invention), or a pharmaceutically acceptable salt thereof. Methods for determining safe and effective administration of compounds which are pharmaceutically active, for example, a compound of Formula A-a, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention can be administered at a total daily dosage of up to 1,000 mg, which can be administered in one daily dose or can be divided into two to four doses per day.

In general, in what ever form administered, the dosage form administered will contain an amount of at least one compound of the invention, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include compounds with dopaminergic activity, for example, i) L-DOPA; ii) DOPA decarboxylase inhibitors; and iii) COMT inhibitors.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

In the examples that follow certain of the exemplified compounds are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

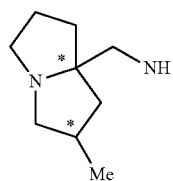

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

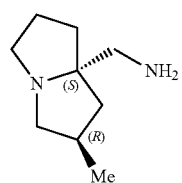

ABC-1

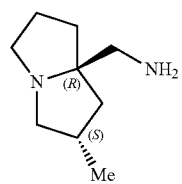

ABC-2

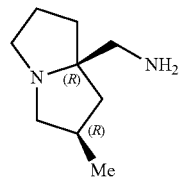

ABC-3

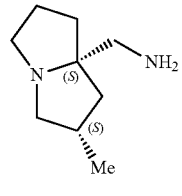

ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine, In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where isomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S7aS)-2-methylhexahydro-1H-pyrrolizin-7a-yl)methanamine".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as limiting the invention to these specifically exemplified compounds.

GENERAL SCHEMES AND EXAMPLES

Intermediate A1

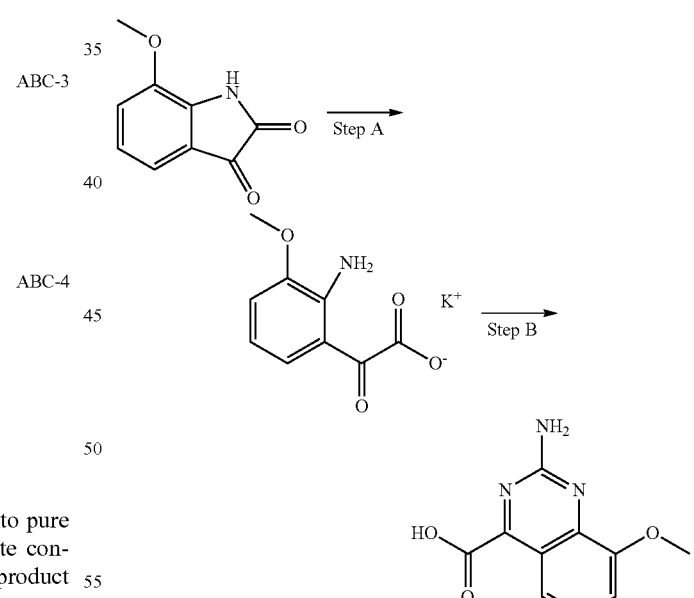

Intermediate A1

Step A: potassium 2-(2-amino-3-methoxy-phenyl)-2-oxo-acetate

To a stirring suspension of 7-methoxyindoline-2,3-dione (11 g, 64 mmol) in water (64 ml) was added potassium hydroxide (5.5 g, 80 mmol). The reaction mixture was stirred at 40° C. for 5h. The reaction mixture was allowed to cool to room temperature, the precipitate was removed through filtration and the filtrate lyophilized to give the title compound as a white solid. The product was used without purification in the next step. LC/MS=196 [M+1].

Step B:
2-amino-8-methoxy-quinazoline-4-carboxylic acid

Sodium hydroxide (4 g, 60 mmol) was added to a stirring suspension of guanidine hydrochloride (5.5 g, 60 mmol) in ethanol (100 ml). The resulting suspension was stirred at room temperature for 2h. The dark orange suspension was filtered and the filtrate was concentrated in vacuo. Potassium 2-(2-amino-3-methoxyphenyl)-2-oxoacetate (6 g, 26 mmol) was added and the solids were mixed. The mixture was then heated to 130° C. for overnight and then allowed to cool to room temperature. The brown mixture was filtered to remove particulates and the filtrate was acidified to pH-2 through addition of HCl (1M). The precipitated product was collected by filtration and dried overnight under vacuum to give the title compound as a mixture which was used in the next step. 1H NMR (DMSO-d): δ 3.9 (s, 3 H), 7.0 (s, 2H), 7.1-7.2 (m, 2 H), 7.4-7.5 (m, 1 H).

Table I

The following compounds were prepared according to the general procedure provided to synthesize intermediate A1, substituting the appropriate indoline-2,3-dione acid for 7-methoxyindoline-2,3-dione. The starting materials are either commercially available or may be prepared from commercially available reagents using conventional reactions well known in the art.

TABLE I

| Intermediate | Structure | Name | LC/MS [M + 1] |
|---|---|---|---|
| A2 | 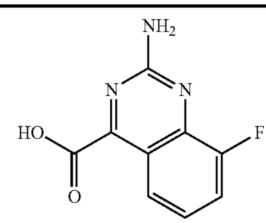 | 2-amino-8-fluoro-quinazoline-4-carboxylic acid | 208 |
| A3 | 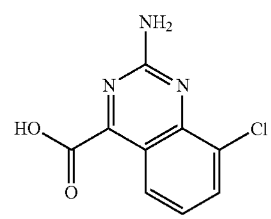 [SMILES: Nc1nc(C(=O)O)c2cccc(Cl)c2n1] | 2-amino-8-chloro-quinazoline-4-carboxylic acid | 224 |
| A4 | 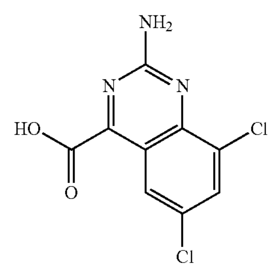 [SMILES: Nc1nc(C(=O)O)c2cc(Cl)cc(Cl)c2n1] | 2-amino-6,8-dichloro-quinazoline-4-carboxylic acid | 258 |
| A5 | 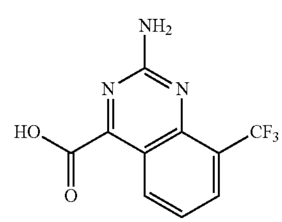 [SMILES: Nc1nc(C(=O)O)c2cccc(C(F)(F)F)c2n1] | 2-amino-8-(trifluoromethyl)quinazoline-4-carboxylic acid | 258 |
| A6 | 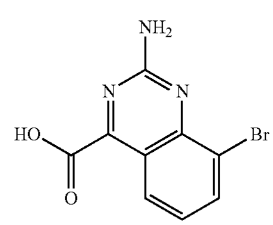 [SMILES: Nc1nc(C(=O)O)c2cccc(Br)c2n1] | 2-amino-8-bromo-quinazoline-4-carboxylic acid | 268 |

TABLE I-continued

| Intermediate | Structure | Name | LC/MS [M + 1] |
|---|---|---|---|
| A7 | 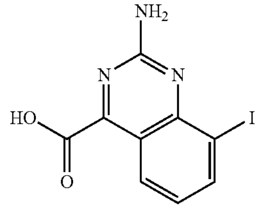 [SMILES: Nc1nc(C(=O)O)c2cccc(I)c2n1] | 2-amino-8-iodo-quinazoline-4-carboxylic acid | 316 |
| A8 | 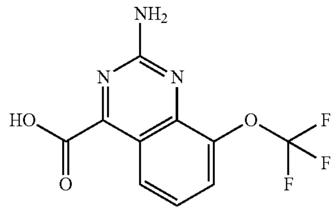 [SMILES: Nc1nc(C(=O)O)c2cccc(OC(F)(F)F)c2n1] | 2-amino-8-(trifluoromethoxy)quinazoline-4-carboxylic acid | 274 |
| A9 | 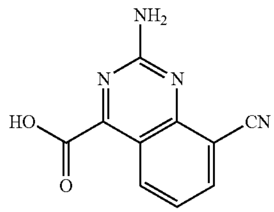 [SMILES: N#Cc1cccc2c(C(=O)O)nc(N)nc12] | 2-amino-8-cyanoquinazoline-4-carboxylic acid | 215 |
| A10 | 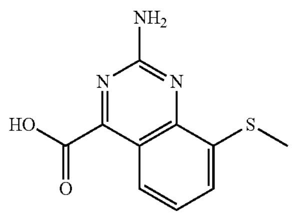 [SMILES: CSc1cccc2c(C(=O)O)nc(N)nc12] | 2-amino-8-(methylthio)quinazoline-4-carboxylic acid | 216 |

Intermediate B1

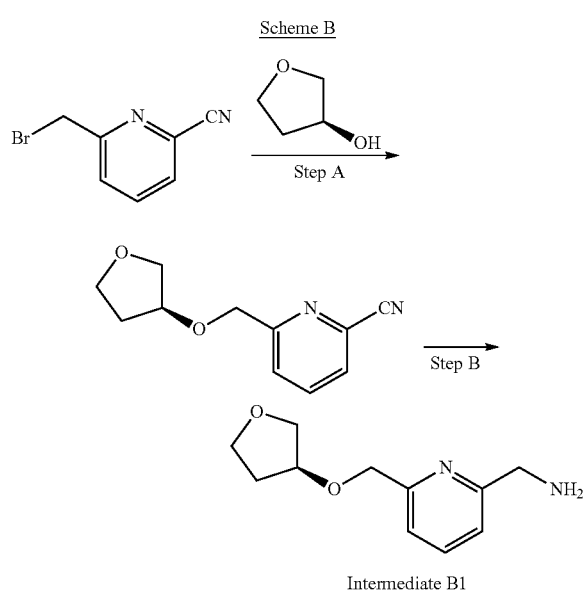

Intermediate B1

Step A: (S)-6-(((tetrahydrofuran-3-yl)oxy)methyl)picolinonitrile

To a suspension of sodium hydride (0.17 g, 4.4 mmol) in tetrahydrofuran (20 mL) was added (S)-tetrahydrofuran-3-ol (0.25 mL, 2.5 mmol). After stirring the reaction mixture at room temperature for 15 minutes, 6-(bromomethyl)picolinonitrile (0.5 g, 2.5 mmol) was added. The reaction mixture was heated to 65° C. for 12h. The reaction mixture was quenched with water (50 mL) and extracted with ethyl acetate (3×50 mL). The combined organic extracts were washed with brine, dried with potassium carbonate, filtered and concentrated in vacuo. The product was purified by column chromatography on silica (0-100% EtOAc/Hexanes) to afford the title compound. LC/MS=205 [M+1].

Step B: (S)-(6-(((tetrahydrofuran-3-yl)oxy)methyl)pyridin-2-yl)methanamine

To a solution of (S)-6-(((tetrahydrofuran-3-yl)oxy)methyl)picolinonitrile (264 mg, 1.3 mmol) in tetrahydrofuran (5 mL) was added lithium aluminum hydride (1.0 M in THF, 4 mL, 4 mmol). The reaction mixture was stirred at room temperature for 16 hours. The reaction mixture was quenched by the addition of water (0.15 mL), 10% sodium hydroxide (0.15 mL), and water (0.45 mL). The reaction mixture was diluted with ethyl acetate, filtered and concentrated in vacuo. The crude residue was dissolved with 1.0 M hydrochloric acid and washed with diethyl ether. It was basified (pH of 14) by the addition of solid sodium hydroxide and extracted with ethyl acetate (3×50 mL). The organic extracts were dried over potassium carbonate, filtered, and concentrated in vacuo to afford the title compound. LC/MS=209 [M+1].

Table II

The following compounds were prepared according to the general procedure provided to synthesize intermediate B1, substituting the appropriate alcohol or thiol for (S)-tetrahydrofuran-3-ol. The starting materials are either commercially available or may be prepared from commercially available reagents using conventional reactions well known in the art.

TABLE II

| Intermediate | Structure | Name | LC/MS [M + 1] |
|---|---|---|---|
| B2 | 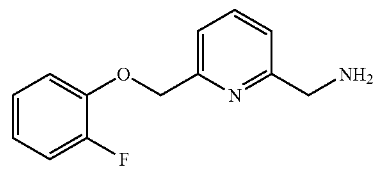 [SMILES: NCc1cccc(COc2ccccc2F)n1] | (6-((2-fluorophenoxy)methyl)pyridin-2-yl)methanamine | 233 |
| B3 | 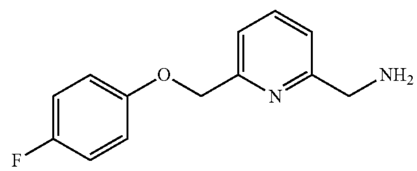 [SMILES: NCc1cccc(COc2ccc(F)cc2)n1] | (6-((4-fluorophenoxy)methyl)pyridin-2-yl)methanamine | 233 |
| B4 | 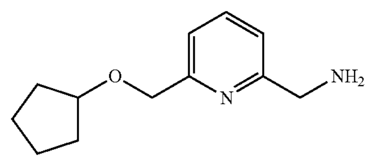 [SMILES: NCc1cccc(COC2CCCC2)n1] | (6-((cyclopentyloxy)methyl)pyridin-2-yl)methanamine | 207 |
| B5 | 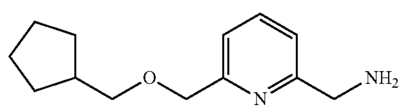 [SMILES: NCc1cccc(COCC2CCCC2)n1] | (6-((cyclopentylmethoxy)methyl)pyridin-2-yl)methanamine | 221 |
| B6 | 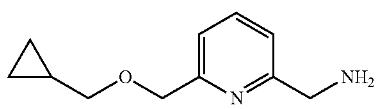 [SMILES: NCc1cccc(COCC2CC2)n1] | (6-((cyclopropylmethoxy)methyl)pyridin-2-yl)methanamine | 193 |
| B7 | 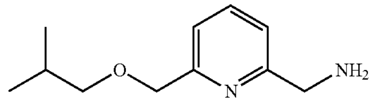 | (6-(isobutoxymethyl)pyridin-2-yl)methanamine | 195 |
| B8 | 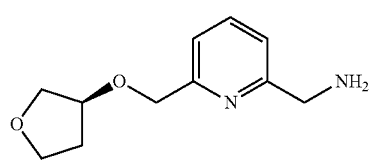 [SMILES: NCc1cccc(CO[C@H]2CCOC2)n1] | (S)-(6-(((tetrahydrofuran-3-yl)oxy)methyl)pyridin-2-yl)methanamine | 209 |
| B9 | 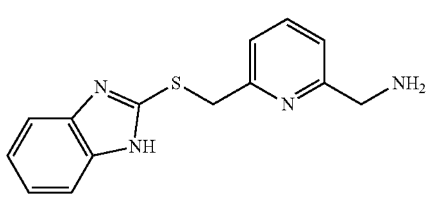 [SMILES: NCc1cccc(CSc2nc3ccccc3[nH]2)n1] | [6-(1H-benzimidazol-2-ylsulfanylmethyl)-2-pyridyl]methanamine | 271 |

Example 1

2-amino-N-((6-(2-hydroxypropan-2-yl)-3-methoxy-pyridin-2-yl)methyl)-8-methoxyquinazoline-4-carboxamide

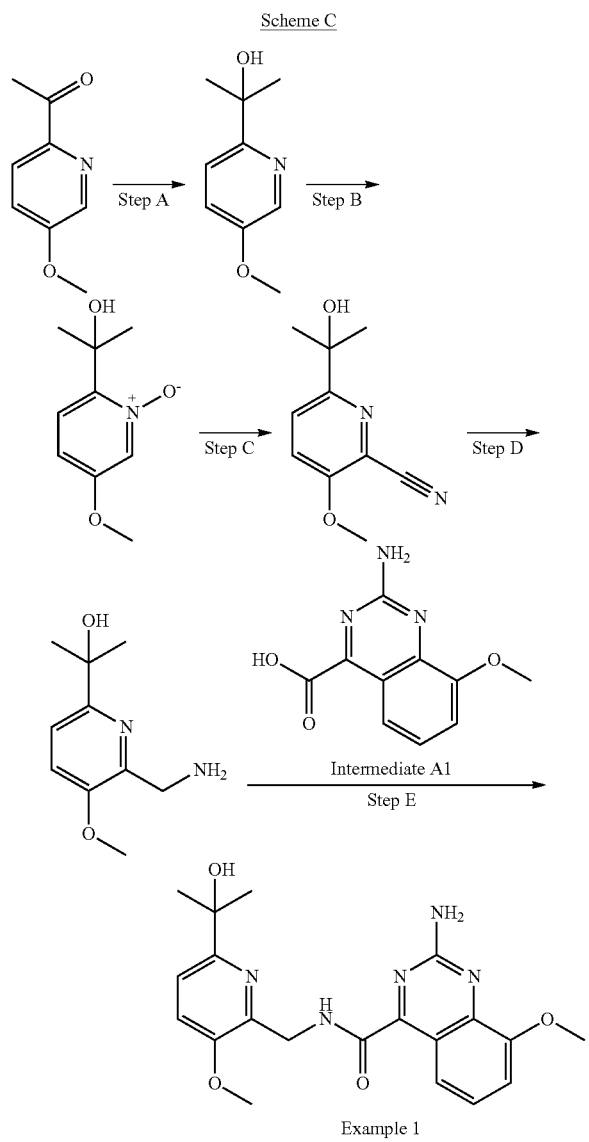

Step A: 2-(5-methoxypyridin-2-yl)propan-2-ol 1-(5-methoxypyridin-2-yl)ethanone (1 g, 7 mmol) in THF (22 ml) was cooled to 0° C. and added to it methylmagnesium bromide (3M in dibutyl ether, 4.5 ml, 13 mmol) dropwise with stirring. The reaction mixture was allowed to warm to room temperature and stir for 2h. The reaction was quenched with saturated aqueous ammonium chloride and the product was extracted with DCM (3×30 mL). The organics were concentrated in vacuo and the product was purified by column chromatography on silica (0-100% EtOAc/Hexanes) to give the title compound. LCMS=168 [M+1].

Step B: 2-(2-hydroxypropan-2-yl)-5-methoxypyridine 1-oxide

A solution of 2-(5-methoxypyridin-2-yl)propan-2-ol (374 mg, 2 mmol) in DCM (4 ml) was cooled to 0° C. and mCPBA (0.4 g, 2.5 mmol) was added to it. The reaction mixture was stirred overnight at room temperature. Potassium carbonate (0.6 g, 4 mmol) was added and the reaction mixture was stirred for 3h. The white suspension was filtered and the filtercake was rinsed with copious amounts of DCM. The filtrate was concentrated in vacuo to give the title compound as a white solid. The product was carried on to the next step without purification. LC/MS=184 [M+1].

Step C: 6-(2-hydroxypropan-2-yl)-3-methoxypicolinonitrile

To a solution of 2-(2-hydroxypropan-2-yl)-5-methoxypyridine 1-oxide (390 mg, 2 mmol) in DCM (8.5 ml) was added dimethylcarbamoyl chloride (0.6 ml, 6 mmol) followed by trimethylsilyl cyanide (0.9 ml, 6 mmol). The reaction mixture was heated to reflux with stirring overnight. The reaction mixture was allowed to cool to room temperature and was concentrated in vacuo. The crude residue was dissolved in methanol (20 mL) and HCl (5 ml, 5N in dioxane) was added. The reaction mixture was stirred for 30 min before being concentrated in vacuo. The product was purified by column chromatography on silica (0-100% EtOAc/Hexanes) to give the titled compound. LC/MS=193 [M+1].

Step D: 2-(6-(aminomethyl)-5-methoxypyridin-2-yl)propan-2-ol 6-(2-hydroxypropan-2-yl)-3-methoxypicolinonitrile (200 mg, 1 mmol) in THF (10 mL) was cooled to 0° C. and lithium aluminum hydride (1.3 mL, 2.6 mmol, 2M in THF) was slowly added to it. The reaction mixture was stirred at room temperature for 2h. Water (120 µL), diethylether (10 mL), NaOH (3N aqueous, 120 µL), and water (340 µL) were added slowly in the indicated order while the reaction mixture was stirred at 0° C. The reaction mixture was allowed to stir for 30 min warming to room temperature before removal of the precipitate salts by filtration. The filtrate was concentrated in vacuo to give the title compound. The amine was carried to the next step without purification. LC/MS=197 [M+1].

Step E: 2-amino-N-((6-(2-hydroxypropan-2-yl)-3-methoxypyridin-2-yl)methyl)-8-methoxyquinazoline-4-carboxamide (Example 1)

2-amino-8-methoxyquinazoline-4-carboxylic acid (100 mg, 0.5 mmol), PyCloP (190 mg, 0.5 mmol), and 2-(6-(aminomethyl)-5-methoxypyridin-2-yl)propan-2-ol (90 mg, 0.5 mmol) were mixed into DMF (4.5 ml). To the stirring suspension was added DIEA (240 µl, 1.376 mmol). The reaction mixture was stirred overnight at room temperature. The reaction mixture was diluted with water (25 ml), saturated with sodium chloride and the product extracted with EtOAc (3×40 mL). The organics were concentrated in vacuo. The product was purified by column chromatography on silica (0-100% EtOAc/Hexanes, 0-20% MeOH/EtOAc). The isolated product was crystallized from IPA/Heptane (30%) to give the title compound as a light yellow solid. LC/MS=398 [M+1]. 1H NMR (CHCl3-d): δ 1.61 (s, 6 H), 3.95 (s, 3 H), 4.07 (s, 3 H), 4.82 (d, 2 H), 5.20 (s, 1 H), 5.62 (s, 2 H), 7.14 (d, 1 H), 7.28-7.25 (m, 2 H), 7.33 (d, 1 H), 8.71 (d, 1 H), 9.29 (s, 1 H).

TABLE IIIa

| Ex. | Structure | Name | LC/MS [M + 1] | A2a Ki (nM) |
|---|---|---|---|---|
| Example 1 | 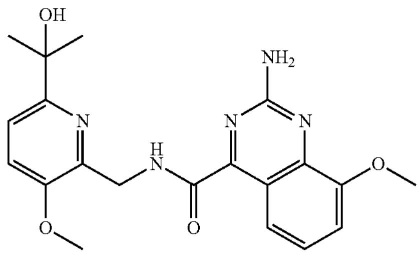 [SMILES: COc1ccc(C(C)(C)O)nc1CNC(=O)c1nc(N)nc2c(OC)cccc12] | 2-amino-N-[[6-(1-hydroxy-1-methyl-ethyl)-3-methoxy-2-pyridyl]methyl]-8-methoxy-quinazoline-4-carboxamide | 398 | 10 |

Table IIIb

The following examples (2-101) were prepared according to the general procedure provided to synthesize example 1, substituting the appropriate quinazoline carboxylic acid for 2-amino-8-methoxyquinazoline-4-carboxylic acid and substituting either the appropriate nitrile for 6-(2-hydroxypropan-2-yl)-3-methoxypicolinonitrile or the appropriate amine for 2-(6-(aminomethyl)-5-methoxypyridin-2-yl)propan-2-ol. The starting materials are commercially available, described above, or may be prepared from commercially available reagents using conventional reactions well known in the art. Racemic mixtures were resolved by chiral chromatography.

TABLE IIIb

| Ex. | Structure | Name | LC/MS [M + 1] | A2a Ki (nM) |
|---|---|---|---|---|
| 2 | 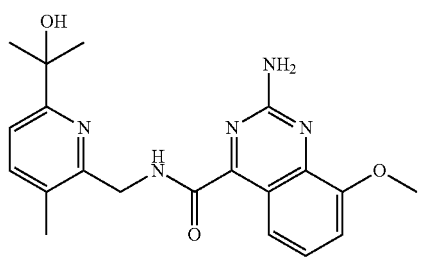 | 2-amino-N-[[6-(1-hydroxy-1-methyl-ethyl)-3-methyl-2-pyridyl]methyl]-8-methoxy-quinazoline-4-carboxamide | 382 | 0.6 |
| 3 | 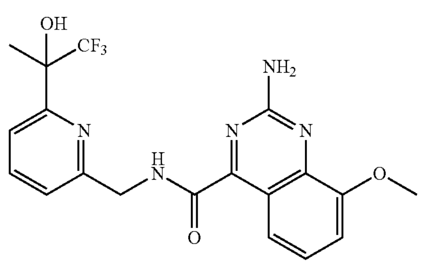 | 2-amino-8-methoxy-N-[[6-(2,2,2-trifluoro-1-hydroxy-1-methyl-ethyl)-2-pyridyl]methyl]quinazoline-4-carboxamide (+ or −) | 422 | 0.5 |
| 4 | 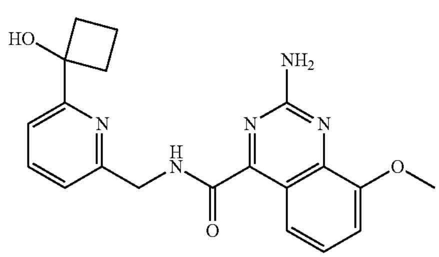 [SMILES: COc1cccc2c(C(=O)NCc3cccc(C4(O)CCC4)n3)nc(N)nc12] | 2-amino-N-[[6-(1-hydroxycyclobutyl)-2-pyridyl]methyl]-8-methoxy-quinazoline-4-carboxamide | 380 | 0.6 |

TABLE IIIb-continued

| Ex. | Structure | Name | LC/MS [M + 1] | A2a Ki (nM) |
|---|---|---|---|---|
| 5 | 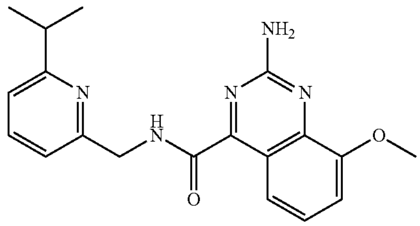 [SMILES: COc1cccc2c(C(=O)NCc3cccc(C(C)C)n3)nc(N)nc12] | 2-amino-N-[(6-isopropyl-2-pyridyl)methyl]-8-methoxy-quinazoline-4-carboxamide | 352 | 0.2 |
| 6 | 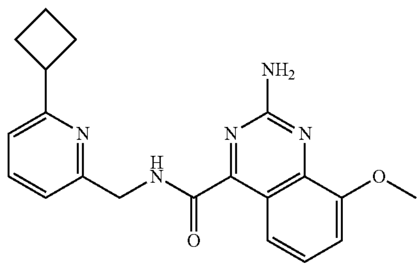 [SMILES: COc1cccc2c(C(=O)NCc3cccc(C4CCC4)n3)nc(N)nc12] | 2-amino-N-[(6-cyclobutyl-2-pyridyl)methyl]-8-methoxy-quinazoline-4-carboxamide | 364 | 0.2 |
| 7 | 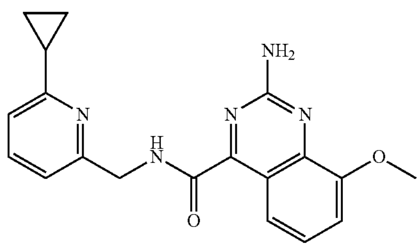 [SMILES: COc1cccc2c(C(=O)NCc3cccc(C4CC4)n3)nc(N)nc12] | 2-amino-N-[(6-cyclopropyl-2-pyridyl)methyl]-8-methoxy-quinazoline-4-carboxamide | 350 | 0.3 |
| 8 | 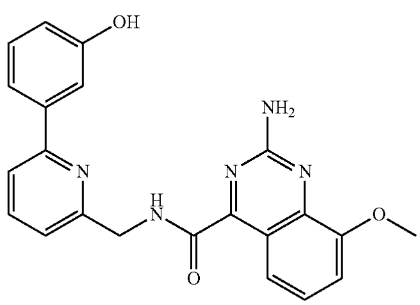 [SMILES: COc1cccc2c(C(=O)NCc3cccc(-c4cccc(O)c4)n3)nc(N)nc12] | 2-amino-N-[[6-(3-hydroxyphenyl)-2-pyridyl]methyl]-8-methoxy-quinazoline-4-carboxamide | 402 | 3.3* |
| 9 | 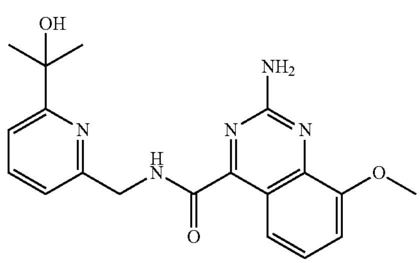 [SMILES: COc1cccc2c(C(=O)NCc3cccc(C(C)(C)O)n3)nc(N)nc12] | 2-amino-N-[[6-(1-hydroxy-1-methyl-ethyl)-2-pyridyl]methyl]-8-methoxy-quinazoline-4-carboxamide | 368 | 0.4 |
| 10 | 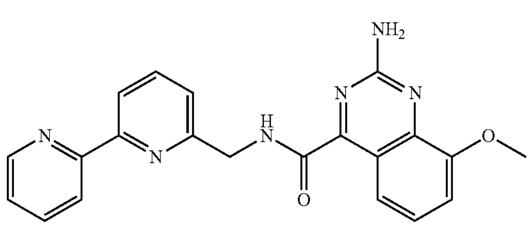 [SMILES: COc1cccc2c(C(=O)NCc3cccc(-c4ccccn4)n3)nc(N)nc12] | 2-amino-8-methoxy-N-[[6-(2-pyridyl)-2-pyridyl]methyl]quinazoline-4-carboxamide | 387 | 1.2 |

TABLE IIIb-continued

| Ex. | Structure | Name | LC/MS [M + 1] | A2a Ki (nM) |
|---|---|---|---|---|
| 11 | 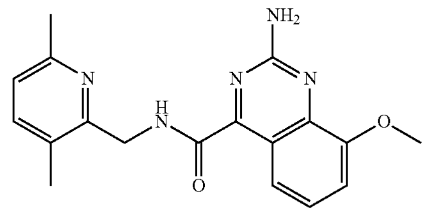 [SMILES: COc1cccc2c(C(=O)NCc3nc(C)ccc3C)nc(N)nc12] | 2-amino-N-[(3,6-dimethyl-2-pyridyl)methyl]-8-methoxy-quinazoline-4-carboxamide | 338 | 0.2 |
| 12 | 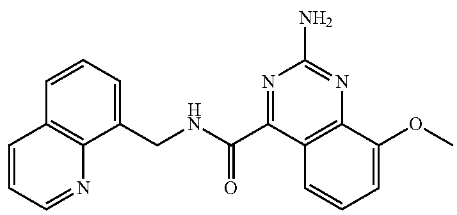 | 2-amino-8-methoxy-N-(8-quinolylmethyl)quinazoline-4-carboxamide | 360 | 0.2 |
| 13 | 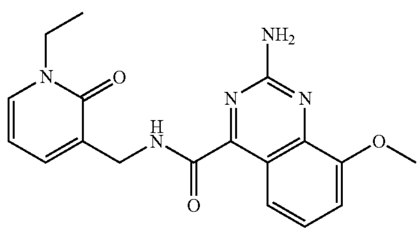 [SMILES: CCn1cccc(CNC(=O)c2nc(N)nc3c(OC)cccc23)c1=O] | 2-amino-N-[(1-ethyl-2-oxo-3-pyridyl)methyl]-8-methoxy-quinazoline-4-carboxamide | 354 | 0.2 |
| 14 | 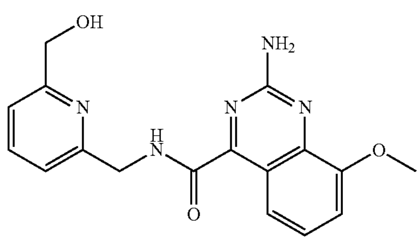 [SMILES: COc1cccc2c(C(=O)NCc3cccc(CO)n3)nc(N)nc12] | 2-amino-N-[[6-(hydroxymethyl)-2-pyridyl]methyl]-8-methoxy-quinazoline-4-carboxamide | 340 | 4.6 |
| 15 | 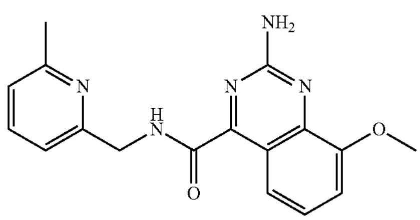 [SMILES: COc1cccc2c(C(=O)NCc3cccc(C)n3)nc(N)nc12] | 2-amino-8-methoxy-N-[(6-methyl-2-pyridyl)methyl]quinazoline-4-carboxamide | 324 | 0.5 |
| 16 | 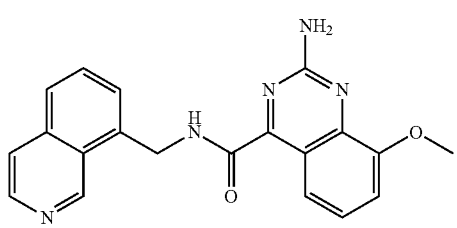 [SMILES: COc1cccc2c(C(=O)NCc3cccc4ccncc34)nc(N)nc12] | 2-amino-N-(8-isoquinolylmethyl)-8-methoxy-quinazoline-4-carboxamide | 360 | 0.3 |
| 17 | 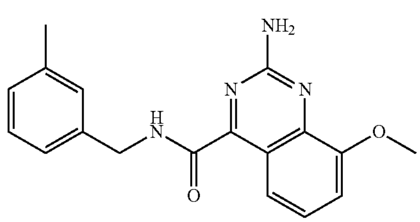 [SMILES: COc1cccc2c(C(=O)NCc3cccc(C)c3)nc(N)nc12] | 2-amino-8-methoxy-N-(m-tolylmethyl)quinazoline-4-carboxamide | 323 | 0.4 |

TABLE IIIb-continued

| Ex. | Structure | Name | LC/MS [M + 1] | A2a Ki (nM) |
|---|---|---|---|---|
| 18 | 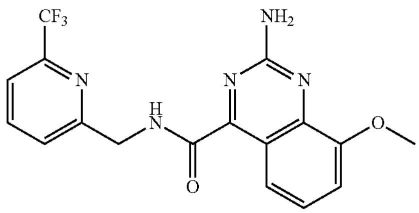 | 2-amino-8-methoxy-N-[[6-(trifluoromethyl)-2-pyridyl]methyl]quinazoline-4-carboxamide | 378 | 0.4 |
| 19 | 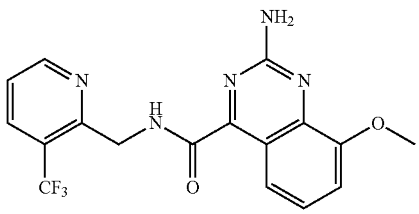 [SMILES: COc1cccc2c(C(=O)NCc3ncccc3C(F)(F)F)nc(N)nc12] | 2-amino-8-methoxy-N-[[3-(trifluoromethyl)-2-pyridyl]methyl]quinazoline-4-carboxamide | 378 | 2.6 |
| 20 | 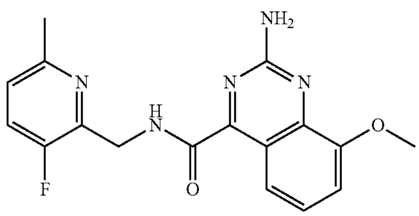 | 2-amino-N-[(3-fluoro-6-methyl-2-pyridyl)methyl]-8-methoxy-quinazoline-4-carboxamide | 342 | 0.5 |
| 21 | 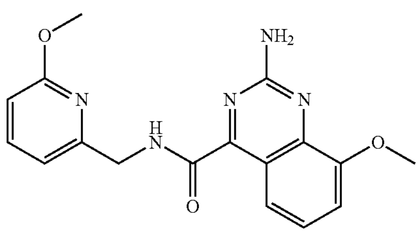 [SMILES: COc1cccc(CNC(=O)c2nc(N)nc3c(OC)cccc23)n1] | 2-amino-8-methoxy-N-[(6-methoxy-2-pyridyl)methyl]quinazoline-4-carboxamide | 340 | 0.8 |
| 22 | 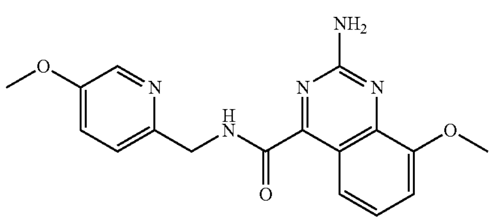 | 2-amino-8-methoxy-N-[(5-methoxy-2-pyridyl)methyl]quinazoline-4-carboxamide | 340 | 7.8 |
| 23 | 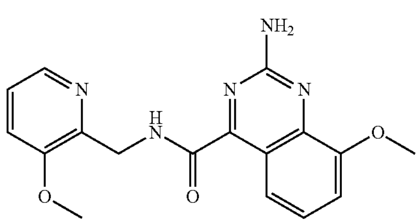 [SMILES: COc1cccnc1CNC(=O)c1nc(N)nc2c(OC)cccc12] | 2-amino-8-methoxy-N-[(3-methoxy-2-pyridyl)methyl]quinazoline-4-carboxamide | 340 | 3.0 |
| 24 | 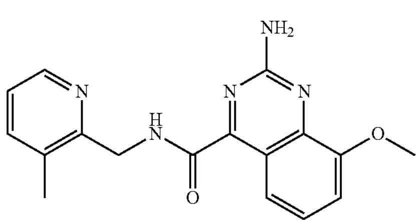 [SMILES: COc1cccc2c(C(=O)NCc3ncccc3C)nc(N)nc12] | 2-amino-8-methoxy-N-[(3-methyl-2-pyridyl)methyl]quinazoline-4-carboxamide | 324 | 0.9 |

TABLE IIIb-continued

| Ex. | Structure | Name | LC/MS [M + 1] | A2a Ki (nM) |
|---|---|---|---|---|
| 25 | 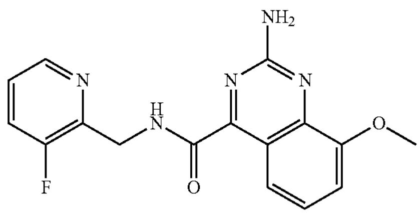 [SMILES: COc1cccc2c(C(=O)NCc3ncccc3F)nc(N)nc12] | 2-amino-N-[(3-fluoro-2-pyridyl)methyl]-8-methoxy-quinazoline-4-carboxamide | 328 | 1.4 |
| 26 | 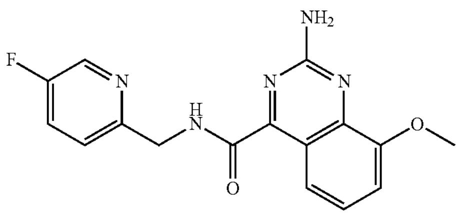 [SMILES: COc1cccc2c(C(=O)NCc3ccc(F)cn3)nc(N)nc12] | 2-amino-N-[(5-fluoro-2-pyridyl)methyl]-8-methoxy-quinazoline-4-carboxamide | 328 | 6.6 |
| 27 | 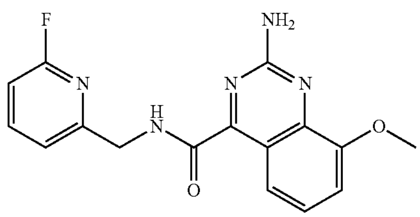 [SMILES: COc1cccc2c(C(=O)NCc3cccc(F)n3)nc(N)nc12] | 2-amino-N-[(6-fluoro-2-pyridyl)methyl]-8-methoxy-quinazoline-4-carboxamide | 328 | 1.5 |
| 28 | 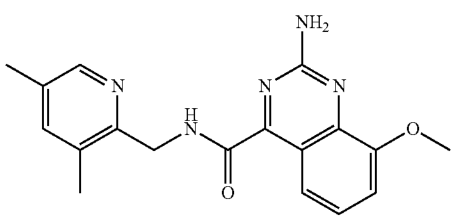 | 2-amino-N-[(3,5-dimethyl-2-pyridyl)methyl]-8-methoxy-quinazoline-4-carboxamide | 338 | 1.5 |
| 29 | 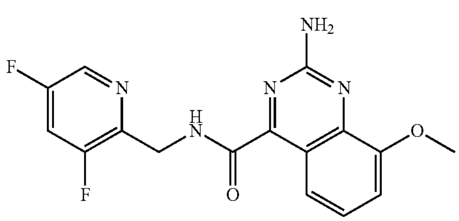 [SMILES: COc1cccc2c(C(=O)NCc3ncc(F)cc3F)nc(N)nc12] | 2-amino-N-[(3,5-difluoro-2-pyridyl)methyl]-8-methoxy-quinazoline-4-carboxamide | 346 | 2.9 |
| 30 | 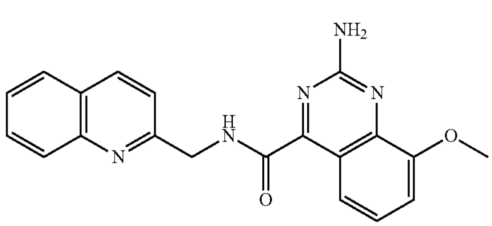 [SMILES: COc1cccc2c(C(=O)NCc3ccc4ccccc4n3)nc(N)nc12] | 2-amino-8-methoxy-N-(2-quinolylmethyl)quinazoline-4-carboxamide | 360 | 1.5 |

TABLE IIIb-continued

| Ex. | Structure | Name | LC/MS [M + 1] | A2a Ki (nM) |
|---|---|---|---|---|
| 31 | 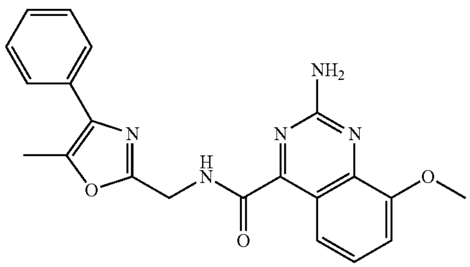 [SMILES: COc1cccc2c(C(=O)NCc3nc(-c4ccccc4)c(C)o3)nc(N)nc12] | 2-amino-8-methoxy-N-[(5-methyl-4-phenyl-oxazol-2-yl)methyl]quinazoline-4-carboxamide | 390 | 1.6 |
| 32 | 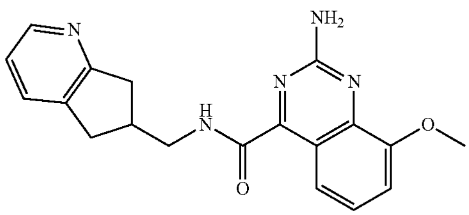 [SMILES: COc1cccc2c(C(=O)NCC3Cc4cccnc4C3)nc(N)nc12] | 2-amino-N-(6,7-dihydro-5H-cyclopenta[b]pyridin-7-yl)-8-methoxy-quinazoline-4-carboxamide (+ or −) | 336 | 1.8 |
| 33 | 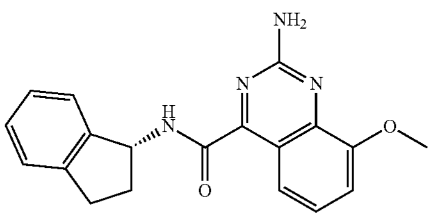 [SMILES: COc1cccc2c(C(=O)N[C@@H]3CCc4ccccc43)nc(N)nc12] | 2-amino-N-[(1R)-indan-1-yl]-8-methoxy-quinazoline-4-carboxamide | 335 | 5.3 |
| 34 | 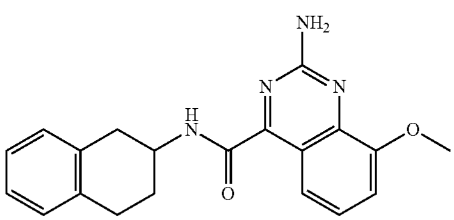 [SMILES: COc1cccc2c(C(=O)NC3CCc4ccccc4C3)nc(N)nc12] | 2-amino-8-methoxy-N-[2-tetralin-2-yl]quinazoline-4-carboxamide (+ or −) | 349 | 20 |
| 35 | 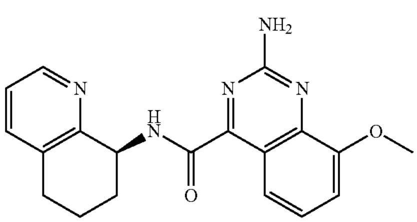 [SMILES: COc1cccc2c(C(=O)N[C@H]3CCCc4cccnc43)nc(N)nc12] | 2-amino-8-methoxy-N-[(8S)-5,6,7,8-tetrahydroquinolin-8-yl]quinazoline-4-carboxamide | 350 | 180 |
| 36 | 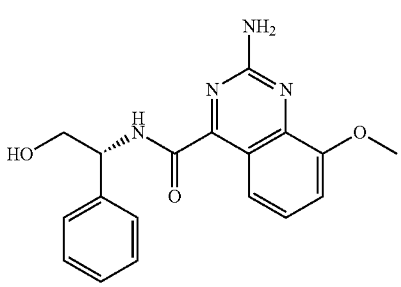 [SMILES: COc1cccc2c(C(=O)N[C@@H](CO)c3ccccc3)nc(N)nc12] | 2-amino-N-[(1R)-2-hydroxy-1-phenyl-ethyl]-8-methoxy-quinazoline-4-carboxamide | 339 | 2.6 |

TABLE IIIb-continued

| Ex. | Structure | Name | LC/MS [M + 1] | A2a Ki (nM) |
|---|---|---|---|---|
| 37 | 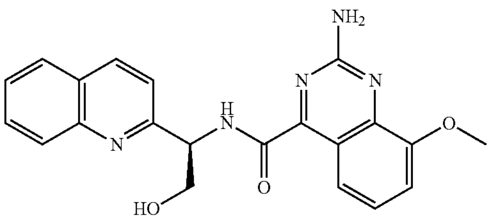 [SMILES: COc1cccc2c(C(=O)N[C@@H](CO)c3ccc4ccccc4n3)nc(N)nc12] | 2-amino-N-[(1R)-2-hydroxy-1-(2-quinolyl)ethyl]-8-methoxy-quinazoline-4-carboxamide | 390 | 8.3 |
| 38 | 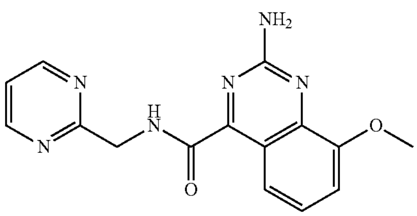 [SMILES: COc1cccc2c(C(=O)NCc3ncccn3)nc(N)nc12] | 2-amino-8-methoxy-N-(pyrimidin-2-ylmethyl)quinazoline-4-carboxamide | 311 | 43 |
| 39 | 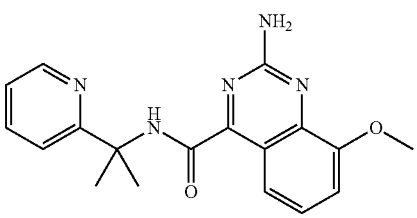 [SMILES: COc1cccc2c(C(=O)NC(C)(C)c3ccccn3)nc(N)nc12] | 2-amino-8-methoxy-N-[1-methyl-1-(2-pyridyl)ethyl]quinazoline-4-carboxamide | 338 | 415 |
| 40 | 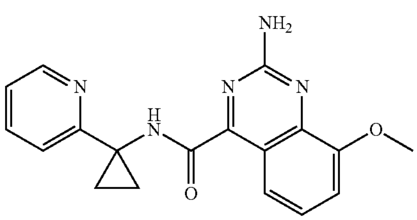 [SMILES: COc1cccc2c(C(=O)NC3(c4ccccn4)CC3)nc(N)nc12] | 2-amino-8-methoxy-N-[1-(2-pyridyl)cyclopropyl]quinazoline-4-carboxamide | 336 | 929 |
| 41 | 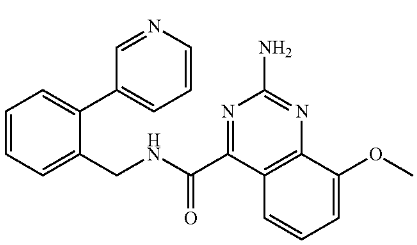 [SMILES: COc1cccc2c(C(=O)NCc3ccccc3-c3cccnc3)nc(N)nc12] | 2-amino-8-methoxy-N-[[2-(3-pyridyl)phenyl]methyl]quinazoline-4-carboxamide | 386 | 9.2* |
| 42 | 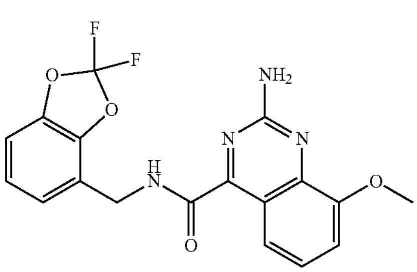 [SMILES: COc1cccc2c(C(=O)NCc3cccc4c3OC(F)(F)O4)nc(N)nc12] | 2-amino-N-[(2,2,-difluoro-1,3-benzodioxol-4-yl)methyl]-8-methoxy-quinazoline-4-carboxamide | 389 | 5.3* |

TABLE IIIb-continued

| Ex. | Structure | Name | LC/MS [M + 1] | A2a Ki (nM) |
|---|---|---|---|---|
| 43 | 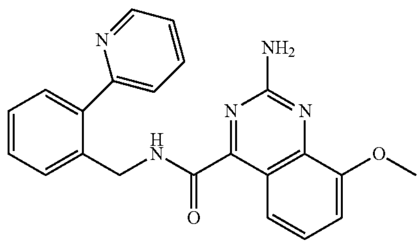 [SMILES: COc1cccc2c(C(=O)NCc3ccccc3-c3ccccn3)nc(N)nc12] | 2-amino-8-methoxy-N-[[2-(2-pyridyl)phenyl]methyl]quinazoline-4-carboxamide | 386 | 2.3* |
| 44 | 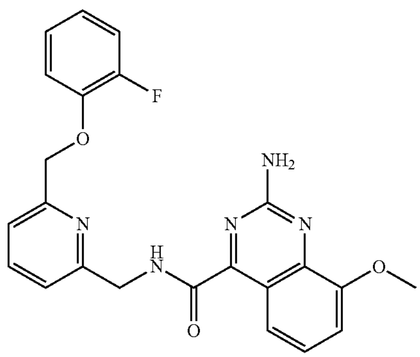 [SMILES: COc1cccc2c(C(=O)NCc3cccc(COc4ccccc4F)n3)nc(N)nc12] | 2-amino-N-[[6-[(2-fluorophenoxy)methyl]-2-pyridyl]methyl]-8-methoxy-quinazoline-4-carboxamide | 434 | 0.2 |
| 45 | 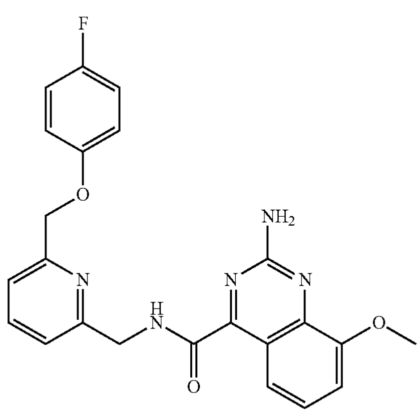 [SMILES: COc1cccc2c(C(=O)NCc3cccc(COc4ccc(F)cc4)n3)nc(N)nc12] | 2-amino-N-[[6-[(4-fluorophenoxy)methyl]-2-pyridyl]methyl]-8-methoxy-quinazoline-4-carboxamide | 434 | 0.3 |
| 46 | 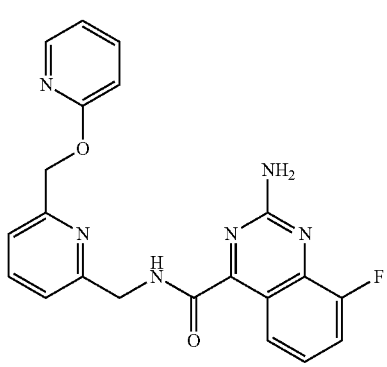 [SMILES: Nc1nc(C(=O)NCc2cccc(COc3ccccn3)n2)c2cccc(F)c2n1] | 2-amino-8-fluoro-N-[[6-(2-pyridyloxymethyl)-2-pyridyl]methyl]quinazoline-4-carboxamide | 405 | 2.2 |

TABLE IIIb-continued

| Ex. | Structure | Name | LC/MS [M + 1] | A2a Ki (nM) |
|---|---|---|---|---|
| 47 | 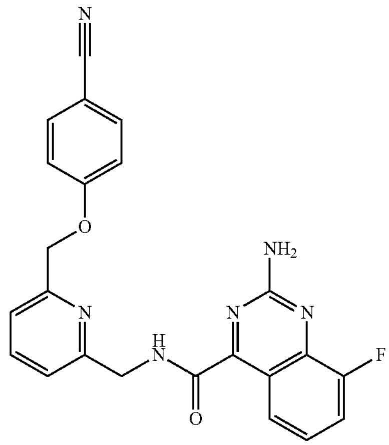 [SMILES: N#Cc1ccc(OCc2cccc(CNC(=O)c3nc(N)nc4c(F)cccc34)n2)cc1] | 2-amino-N-[[6-[(4-cyanophenoxy)methyl]-2-pyridyl]methyl]-8-fluoro-quinazoline-4-carboxamide | 429 | 3.8* |
| 48 | 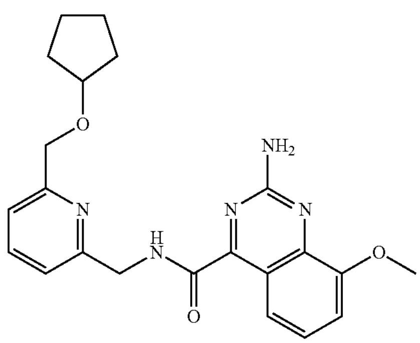 [SMILES: COc1cccc2c(C(=O)NCc3cccc(COC4CCCC4)n3)nc(N)nc12] | 2-amino-N-[[6-(cyclopentoxymethyl)-2-pyridyl]methyl]-8-methoxy-quinazoline-4-carboxamide | 408 | 0.5 |
| 49 | 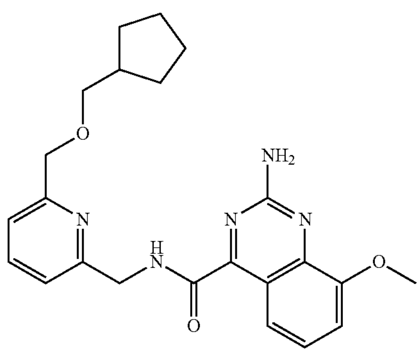 [SMILES: COc1cccc2c(C(=O)NCc3cccc(COCC4CCCC4)n3)nc(N)nc12] | 2-amino-N-[[6-(cyclopentylmethoxymethyl)-2-pyridyl]methyl]-8-methoxy-quinazoline-4-carboxamide | 422 | 0.5 |
| 50 | 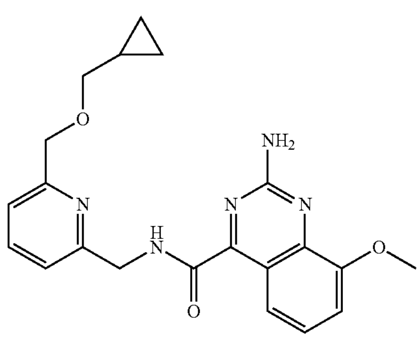 [SMILES: COc1cccc2c(C(=O)NCc3cccc(COCC4CC4)n3)nc(N)nc12] | 2-amino-N-[[6-(cyclopropylmethoxymethyl)-2-pyridyl]methyl]-8-methoxy-quinazoline-4-carboxamide | 394 | 1.3 |

TABLE IIIb-continued

| Ex. | Structure | Name | LC/MS [M + 1] | A2a Ki (nM) |
|---|---|---|---|---|
| 51 | 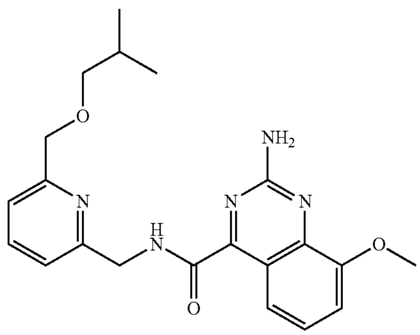 [SMILES: COc1cccc2c(C(=O)NCc3cccc(COCC(C)C)n3)nc(N)nc12] | 2-amino-N-[[6-(isobutoxymethyl)-2-pyridyl]methyl]-8-methoxy-quinazoline-4-carboxamide | 396 | 1.9 |
| 52 | 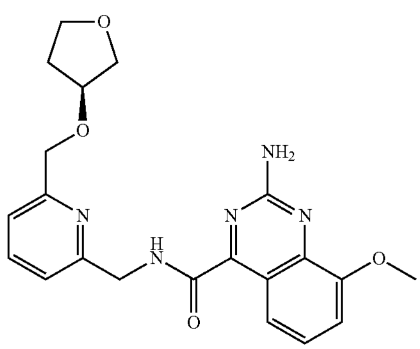 [SMILES: COc1cccc2c(C(=O)NCc3cccc(CO[C@H]4CCOC4)n3)nc(N)nc12] | 2-amino-8-methoxy-N-[[6-[[(3S)-tetrahydrofuran-3-yl]oxymethyl]-2-pyridyl]methyl]quinazoline-4-carboxamide | 410 | 1.1 |
| 53 | 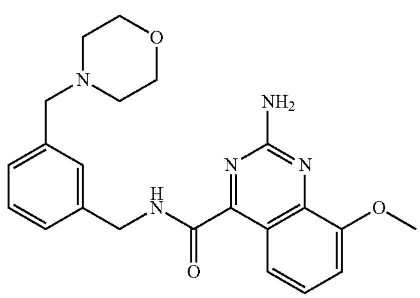 [SMILES: COc1cccc2c(C(=O)NCc3cccc(CN4CCOCC4)c3)nc(N)nc12] | 2-amino-8-methoxy-N-[[3-(morpholinomethyl)phenyl]methyl]quinazoline-4-carboxamide | 408 | 7.1 |
| 54 | 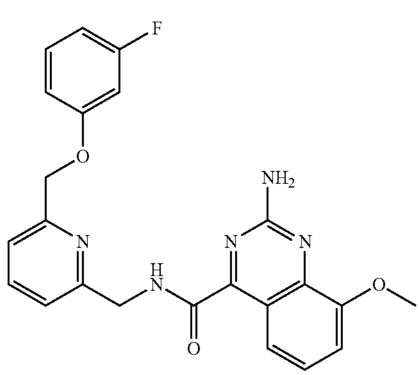 [SMILES: COc1cccc2c(C(=O)NCc3cccc(COc4cccc(F)c4)n3)nc(N)nc12] | 2-amino-N-[[6-[(3-fluorophenxoy)methyl]-2-pyridyl]methyl]-8-methoxy-quinazoline-4-carboxamide | 434 | 2.1* |

TABLE IIIb-continued

| Ex. | Structure | Name | LC/MS [M + 1] | A2a Ki (nM) |
|---|---|---|---|---|
| 55 | 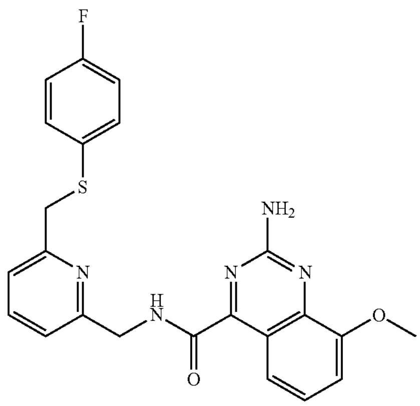 [SMILES: COc1cccc2c(C(=O)NCc3cccc(CSc4ccc(F)cc4)n3)nc(N)nc12] | 2-amino-N-[[6-[(4-fluorophenyl)sulfanylmethyl]-2-pyridyl]methyl]-8-methoxy-quinazoline-4-carboxamide | 450 | 3.2* |
| 56 | 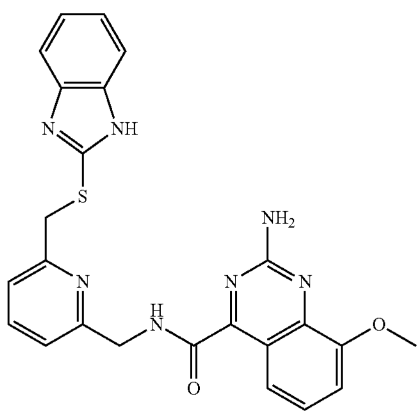 [SMILES: COc1cccc2c(C(=O)NCc3cccc(CSc4nc5ccccc5[nH]4)n3)nc(N)nc12] | 2-amino-N-[[6-(1H-benzimidazol-2-ylsulfanylmethyl)-2-pyridyl]methyl]-8-methoxy-quinazoline-4-carboxamide | 472 | 6.3 |
| 57 | 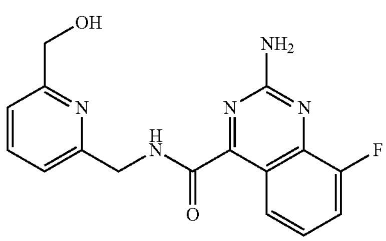 [SMILES: Nc1nc(C(=O)NCc2cccc(CO)n2)c2cccc(F)c2n1] | 2-amino-8-fluoro-N-[[6-(hydroxymethyl)-2-pyridyl]methyl]quinazoline-4-carboxamide | 328 | 9.6 |
| 58 | 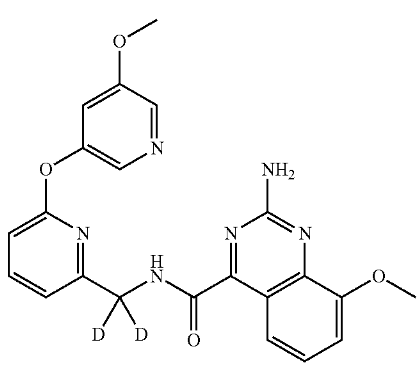 [SMILES: [2H]C([2H])(NC(=O)c1nc(N)nc2c(OC)cccc12)c1cccc(Oc2cncc(OC)c2)n1] | 2-amino-N-[dideuterio-[6-[(5-methoxy-3-pyridyl)oxy]-2-pyridyl]methyl]-8-methoxy-quinazoline-4-carboxamide | 435 | 5.0* |

TABLE IIIb-continued

| Ex. | Structure | Name | LC/MS [M + 1] | A2a Ki (nM) |
|---|---|---|---|---|
| 59 | 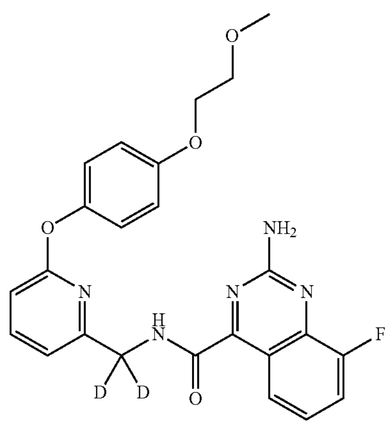 [SMILES: [2H]C([2H])(NC(=O)c1nc(N)nc2c(F)cccc12)c1cccc(Oc2ccc(OCCOC)cc2)n1] | 2-amino-N-[dideuterio-[6-[4-(2-methoxyethoxy)phenoxy]-2-pyridyl]methyl]-8-fluoro-quinazoline-4-carboxamide | 466 | 3.7* |
| 60 | 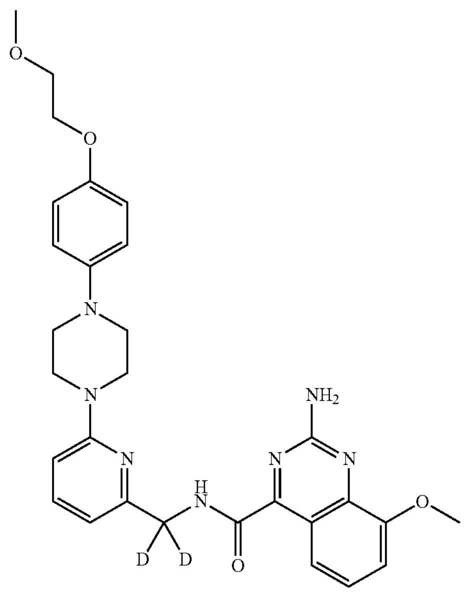 [SMILES: [2H]C([2H])(NC(=O)c1nc(N)nc2c(OC)cccc12)c1cccc(N2CCN(c3ccc(OCCOC)cc3)CC2)n1] | 2-amino-N-[dideuterio-[6-[4-[4-(2-methoxyethoxy)phenyl]piperazin-1-yl]-2-pyridyl]methyl]-8-methoxy-quinazoline-4-carboxamide | 546 | 4.3* |
| 61 | 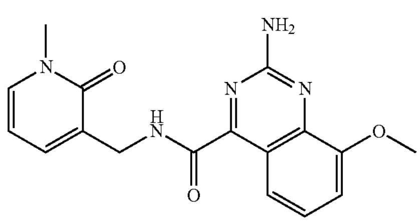 [SMILES: COc1cccc2c(C(=O)NCc3cccn(C)c3=O)nc(N)nc12] | 2-amino-8-methoxy-N-[(1-methyl-2-oxo-3-pyridyl)methyl]quinazoline-4-carboxamide | 340 | 0.9 |
| 62 | 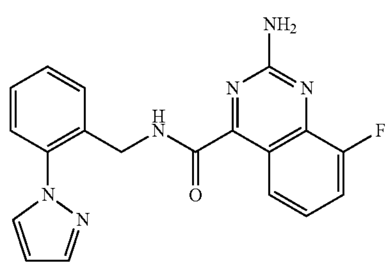 [SMILES: Nc1nc(C(=O)NCc2ccccc2-n2cccn2)c2cccc(F)c2n1] | 2-amino-8-fluoro-N-[(2-pyrazol-1-ylphenyl)methyl]quinazoline-4-carboxamide | 363 | 0.5 |

TABLE IIIb-continued

| Ex. | Structure | Name | LC/MS [M + 1] | A2a Ki (nM) |
|---|---|---|---|---|
| 63 | 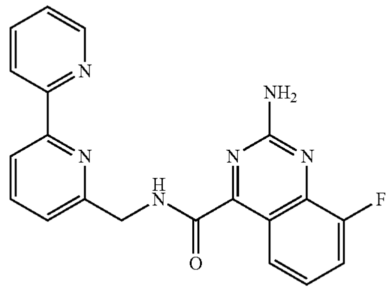 [SMILES: Nc1nc(C(=O)NCc2cccc(-c3ccccn3)n2)c2cccc(F)c2n1] | 2-amino-8-fluoro-N-[[6-(2-pyridyl)-2-pyridyl]methyl]quinazoline-4-carboxamide | 375 | 0.8 |
| 64 | 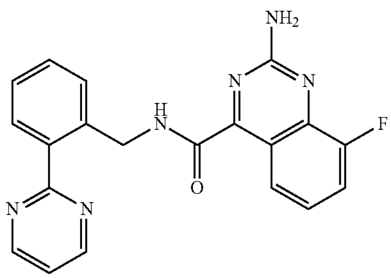 [SMILES: Nc1nc(C(=O)NCc2ccccc2-c2ncccn2)c2cccc(F)c2n1] | 2-amino-8-fluoro-N-[(2-pyrimidin-2-ylphenyl)methyl]quinazoline-4-carboxamide | 375 | 0.9 |
| 65 | 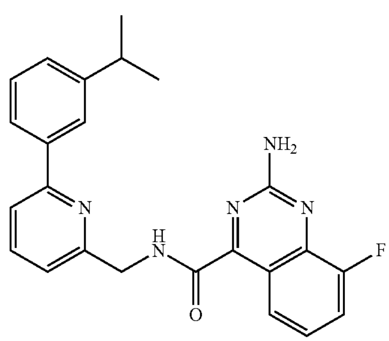 [SMILES: CC(C)c1cccc(-c2cccc(CNC(=O)c3nc(N)nc4c(F)cccc34)n2)c1] | 2-amino-8-fluoro-N-[[6-(3-isopropylphenyl)-2-pyridyl]methyl]quinazoline-4-carboxamide | 416 | 1.0 |
| 66 | 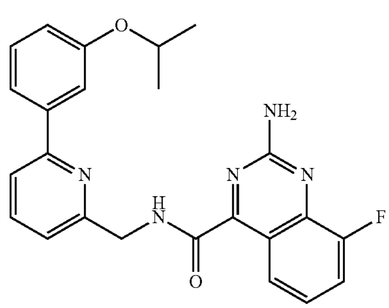 [SMILES: CC(C)Oc1cccc(-c2cccc(CNC(=O)c3nc(N)nc4c(F)cccc34)n2)c1] | 2-amino-8-fluoro-N-[[6-(3-isopropoxyphenyl)-2-pyridyl]methyl]quinazoline-4-carboxamide | 432 | 3.8* |
| 67 | 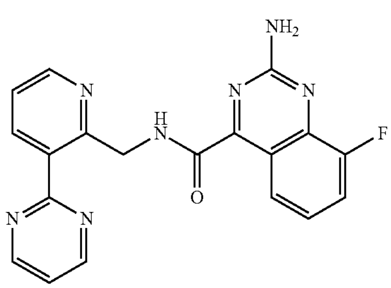 [SMILES: Nc1nc(C(=O)NCc2ncccc2-c2ncccn2)c2cccc(F)c2n1] | 2-amino-8-fluoro-N-[(3-pyrimidin-2-yl-2-pyridyl)methyl]quinazoline-4-carboxamide | 376 | 4.0 |

TABLE IIIb-continued

| Ex. | Structure | Name | LC/MS [M + 1] | A2a Ki (nM) |
|---|---|---|---|---|
| 68 | 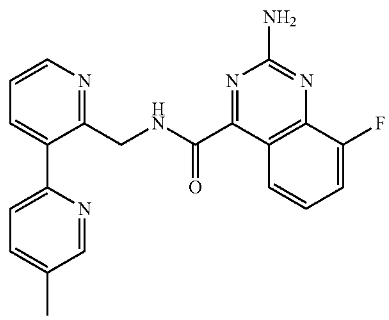 [SMILES: Cc1ccc(-c2cccnc2CNC(=O)c2nc(N)nc3c(F)cccc23)nc1] | 2-amino-8-fluoro-N-[[3-(5-methyl-2-pyridyl)-2-pyridyl]methyl] quinazoline-4-carboxamide | 389 | 9.1* |
| 69 | 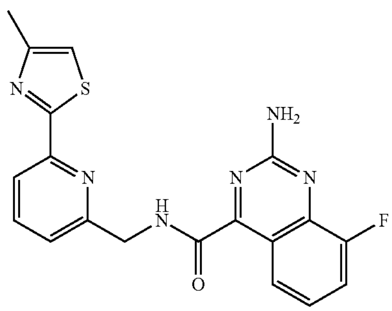 [SMILES: Cc1csc(-c2cccc(CNC(=O)c3nc(N)nc4c(F)cccc34)n2)n1] | 2-amino-8-fluoro-N-[[6-(4-methylthiazol-2-yl)-2-pyridyl]methyl] quinazoline-4-carboxamide | 395 | 4.2 |
| 70 | 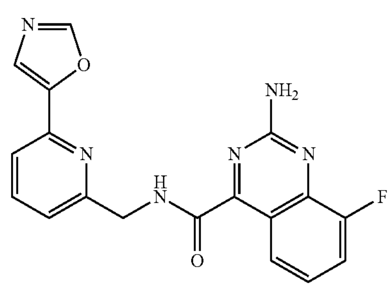 [SMILES: Nc1nc(C(=O)NCc2cccc(-c3cnco3)n2)c2cccc(F)c2n1] | 2-amino-8-fluoro-N-[(6-oxazol-5-yl-2-pyridyl)methyl] quinazoline-4-carboxamide | 365 | 4.5 |
| 71 | 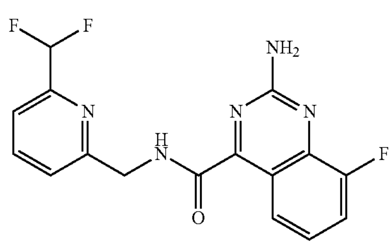 [SMILES: Nc1nc(C(=O)NCc2cccc(C(F)F)n2)c2cccc(F)c2n1] | 2-amino-N-[[6-(difluoromethyl)-2-pyridyl]methyl]-8-fluoro-quinazoline-4-carboxamide | 348 | 3.6 |
| 72 | 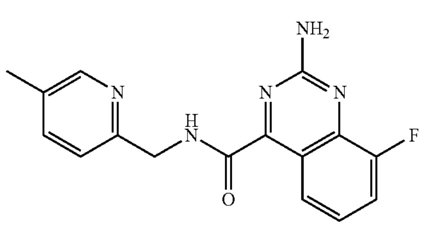 [SMILES: Cc1ccc(CNC(=O)c2nc(N)nc3c(F)cccc23)nc1] | 2-amino-8-fluoro-N-[(5-methyl-2-pyridyl)methyl] quinazoline-4-carboxamide | 312 | 6.1 |

TABLE IIIb-continued

| Ex. | Structure | Name | LC/MS [M + 1] | A2a Ki (nM) |
|---|---|---|---|---|
| 73 | 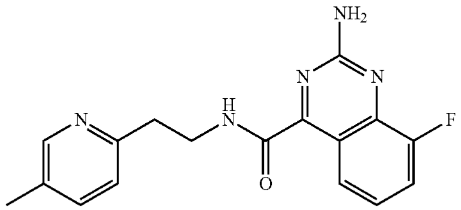 [SMILES: Cc1ccc(CCNC(=O)c2nc(N)nc3c(F)cccc23)nc1] | 2-amino-8-fluoro-N-[2-(5-methyl-2-pyridyl)ethyl]quinazoline-4-carboxamide | 326 | 225 |
| 74 | 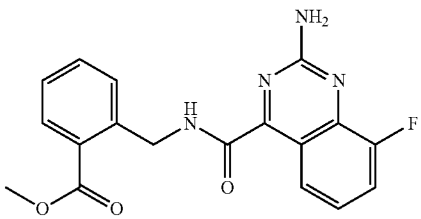 [SMILES: COC(=O)c1ccccc1CNC(=O)c1nc(N)nc2c(F)cccc12] | methyl 2-[[(2-amino-8-fluoro-quinazoline-4-carbonyl)amino]methyl]benzoate | 355 | 2.5* |
| 75 | 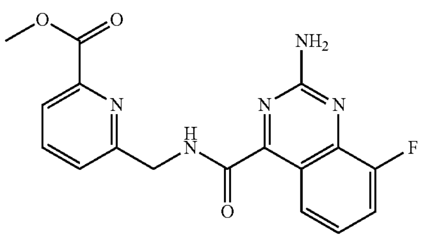 [SMILES: COC(=O)c1cccc(CNC(=O)c2nc(N)nc3c(F)cccc23)n1] | methyl 6-[[(2-amino-8-fluoro-quinazoline-4-carbonyl)amino]methyl]pyridine-2-carboxylate | 356 | 23* |
| 76 | 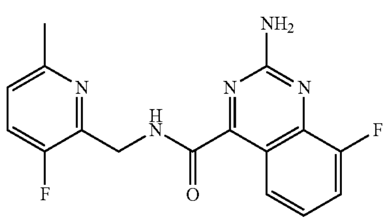 [SMILES: Cc1ccc(F)c(CNC(=O)c2nc(N)nc3c(F)cccc23)n1] | 2-amino-8-fluoro-N-[(3-fluoro-6-methyl-2-pyridyl)methyl]quinazoline-4-carboxamide | 330 | 0.5 |
| 77 | 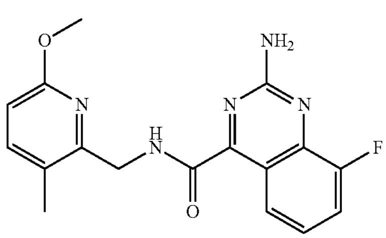 [SMILES: COc1ccc(C)c(CNC(=O)c2nc(N)nc3c(F)cccc23)n1] | 2-amino-8-fluoro-N-[(6-methoxy-3-methyl-2-pyridyl)methyl]quinazoline-4-carboxamide | 342 | 0.8 |
| 78 | 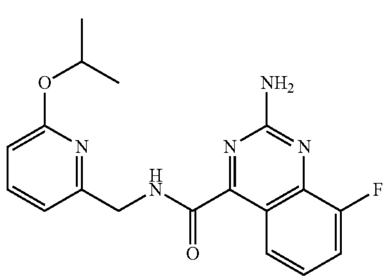 [SMILES: CC(C)Oc1cccc(CNC(=O)c2nc(N)nc3c(F)cccc23)n1] | 2-amino-8-fluoro-N-[(6-isopropoxy-2-pyridyl)methyl]quinazoline-4-carboxamide | 356 | 1.0 |

TABLE IIIb-continued

| Ex. | Structure | Name | LC/MS [M + 1] | A2a Ki (nM) |
|---|---|---|---|---|
| 79 | 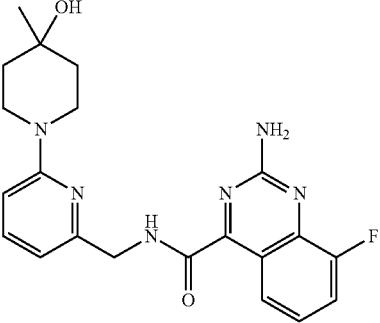 [SMILES: CC1(O)CCN(c2cccc(CNC(=O)c3nc(N)nc4c(F)cccc34)n2)CC1] | 2-amino-8-fluoro-N-[[6-(4-hydroxy-4-methyl-1-piperidyl)-2-pyridyl]methyl]quinazoline-4-carboxamide | 411 | 5.2 |
| 80 | 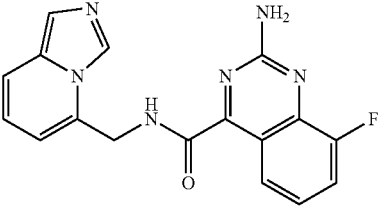 [SMILES: Nc1nc(C(=O)NCc2cccc3cncn23)c2cccc(F)c2n1] | 2-amino-8-fluoro-N-(imidazo[1,5-a]pyridin-5-ylmethyl)quinazoline-4-carboxamide | 337 | 6.2* |
| 81 | 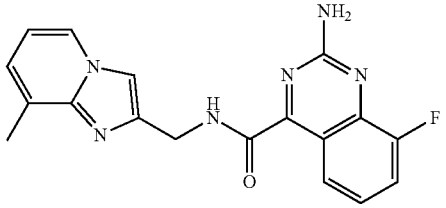 [SMILES: Cc1cccn2cc(CNC(=O)c3nc(N)nc4c(F)cccc34)nc12] | 2-amino-8-fluoro-N-[(8-methylimidazo[1,2-a]pyridin-2-yl)methyl]quinazoline-4-carboxamide | 351 | 6.9 |
| 82 | 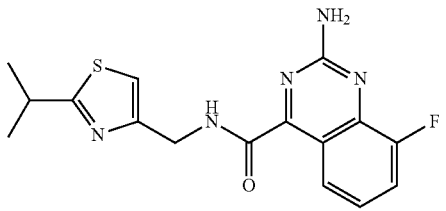 [SMILES: CC(C)c1nc(CNC(=O)c2nc(N)nc3c(F)cccc23)cs1] | 2-amino-8-fluoro-N-[(2-isopropylthiazol-4-yl)methyl]quinazoline-4-carboxamide | 346 | 0.6 |
| 83 | 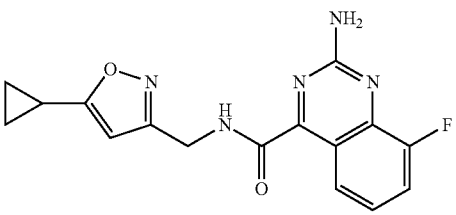 [SMILES: Nc1nc(C(=O)NCc2cc(C3CC3)on2)c2cccc(F)c2n1] | 2-amino-N-[(5-cyclopropylisoxazol-3-yl)methyl]-8-fluoro-quinazoline-4-carboxamide | 328 | 14 |
| 84 | 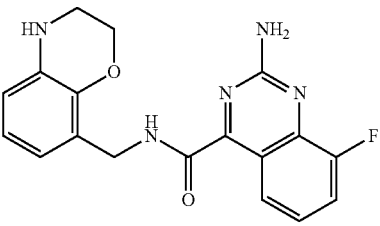 [SMILES: Nc1nc(C(=O)NCc2cccc3c2OCCN3)c2cccc(F)c2n1] | 2-amino-N-(3,4-dihydro-2H-1,4-benzoxazin-8-ylmethyl)-8-fluoro-quinazoline-4-carboxamide | 354 | 5.3 |

TABLE IIIb-continued

| Ex. | Structure | Name | LC/MS [M + 1] | A2a Ki (nM) |
|---|---|---|---|---|
| 85 | 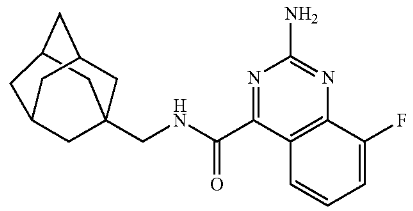 [SMILES: Nc1nc(C(=O)NCC23CC4CC(CC(C4)C2)C3)c2cccc(F)c2n1] | N-(1-adamantylmethyl)-2-amino-8-fluoro-quinazoline-4-carboxamide | 355 | 6.4 |
| 86 | 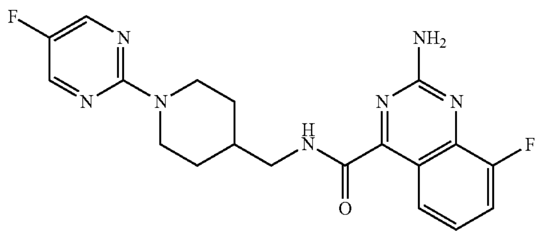 [SMILES: Nc1nc(C(=O)NCC2CCN(c3ncc(F)cn3)CC2)c2cccc(F)c2n1] | 2-amino-8-fluoro-N-[[1-(5-fluoropyrimidin-2-yl)-4-piperidyl]methyl]quinazoline-4-carboxamide | 400 | 8.0 |
| 87 | 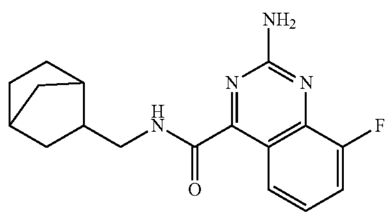 [SMILES: Nc1nc(C(=O)NCC2CC3CCC2C3)c2cccc(F)c2n1] | 2-amino-8-fluoro-N-(norbornan-2-ylmethyl)quinazoline-4-carboxamide | 315 | 32* |
| 88 | 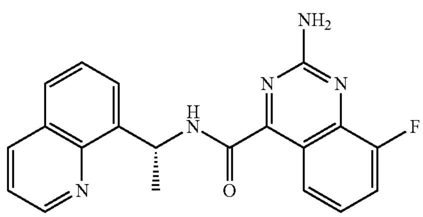 [SMILES: C[C@@H](NC(=O)c1nc(N)nc2c(F)cccc12)c1cccc2cccnc12] | 2-amino-8-fluoro-N-[(1R)-1-(8-quinolyl)ethyl]quinazoline-4-carboxamide | 362 | 6.7 |
| 89 | 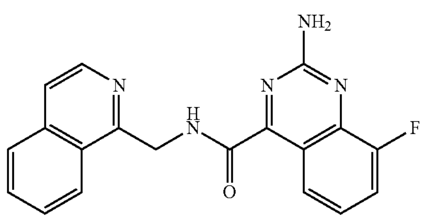 [SMILES: Nc1nc(C(=O)NCc2nccc3ccccc23)c2cccc(F)c2n1] | 2-amino-8-fluoro-N-(isoquinolin-1-ylmethyl)quinazoline-4-carboxamide | 348 | 6.6* |
| 90 | 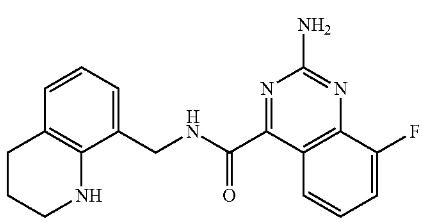 [SMILES: Nc1nc(C(=O)NCc2cccc3c2NCCC3)c2cccc(F)c2n1] | 2-amino-8-chloro-N-((1,2,3,4-tetrahydroquinolin-8-ylmethyl)quinazoline-4-carboxamide | 352 | 3.0 |
| 91 | 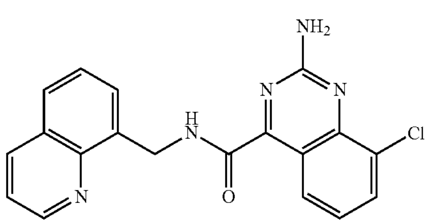 [SMILES: Nc1nc(C(=O)NCc2cccc3cccnc23)c2cccc(Cl)c2n1] | 2-amino-8-chloro-N-(8-quinolylmethyl)quinazoline-4-carboxamide | 364 | 3.0 |

TABLE IIIb-continued

| Ex. | Structure | Name | LC/MS [M + 1] | A2a Ki (nM) |
|---|---|---|---|---|
| 92 | 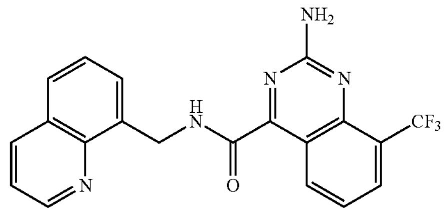 [SMILES: Nc1nc(C(=O)NCc2cccc3cccnc23)c2cccc(C(F)(F)F)c2n1] | 2-amino-N-(8-quinolylmethyl)-8-(trifluoromethyl)quinazoline-4-carboxamide | 398 | 2.3 |
| 93 | 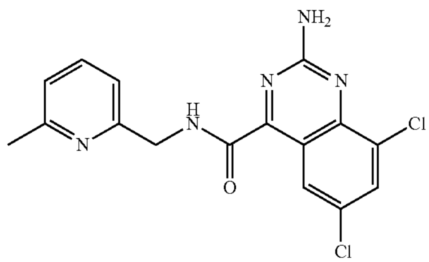 [SMILES: Cc1cccc(CNC(=O)c2nc(N)nc3c(Cl)cc(Cl)cc23)n1] | 2-amino-6,8-dichloro-N-[(6-methyl-2-pyridyl)methyl]quinazoline-4-carboxamide | 362 | 6.5 |
| 94 | 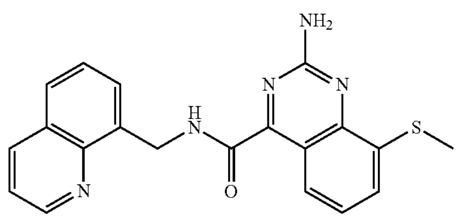 [SMILES: CSc1cccc2c(C(=O)NCc3cccc4cccnc34)nc(N)nc12] | 2-amino-8-methylsulfanyl-N-(8-quinolylmethyl)quinazoline-4-carboxamide | 376 | 7.7* |
| 95 | 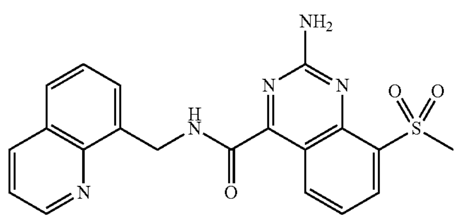 [SMILES: CS(=O)(=O)c1cccc2c(C(=O)NCc3cccc4cccnc34)nc(N)nc12] | 2-amino-8-methylsulfonyl-N-(8-quinolylmethyl)quinazoline-4-carboxamide | 408 | 86 |
| 96 | 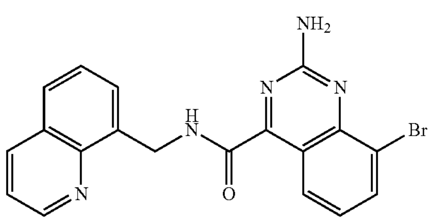 [SMILES: Nc1nc(C(=O)NCc2cccc3cccnc23)c2cccc(Br)c2n1] | 2-amino-8-bromo-N-(8-quinolylmethyl)quinazoline-4-carboxamide | 408 | 0.7* |
| 97 | 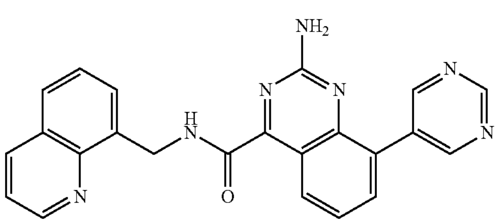 [SMILES: Nc1nc(C(=O)NCc2cccc3cccnc23)c2cccc(-c3cncnc3)c2n1] | 2-amino-8-pyrimidin-5-yl-N-(8-quinolylmethyl)quinazoline-4-carboxamide | 408 | 291 |
| 98 | 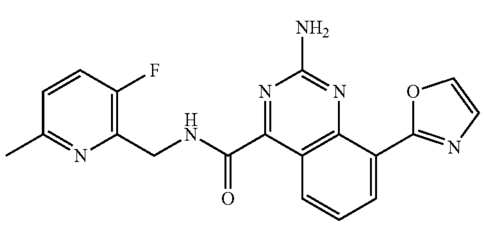 [SMILES: Cc1ccc(F)c(CNC(=O)c2nc(N)nc3c(-c4ncco4)cccc23)n1] | 2-amino-N-[(3-fluoro-6-methyl-2-pyridyl)methyl]-8-oxazol-2-yl-quinazoline-4-carboxamide | 379 | 1.7 |

TABLE IIIb-continued
| Ex. | Structure | Name | LC/MS [M + 1] | A2a Ki (nM) |
|---|---|---|---|---|
| 99 | 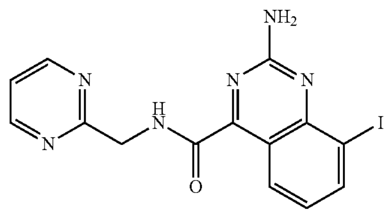 [SMILES: Nc1nc(C(=O)NCc2ncccn2)c2cccc(I)c2n1] | 2-amino-8-iodo-N-(pyrimidin-2-ylmethyl)quinazoline-4-carboxamide | 407 | 229 |
| 100 | 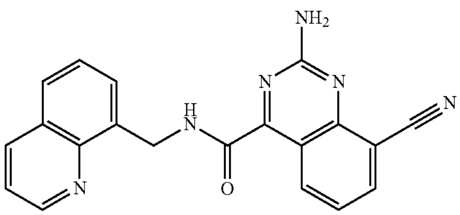 [SMILES: N#Cc1cccc2c(C(=O)NCc3cccc4cccnc34)nc(N)nc12] | 2-amino-8-cyano-N-(8-quinolylmethyl)quinazoline-4-carboxamide | 355 | 2.1 |
| 101 | 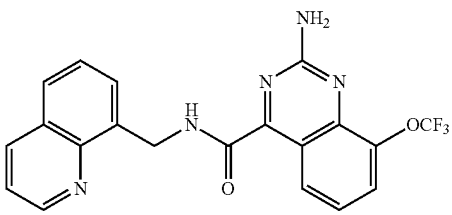 [SMILES: Nc1nc(C(=O)NCc2cccc3cccnc23)c2cccc(OC(F)(F)F)c2n1] | 2-amino-N-(8-quinolylmethyl)-8-(trifluoromethoxy)quinazoline-4-carboxamide | 414 | 0.2 |
Example 102
2-amino-N-[[6-[(3,4-difluorophenyl)methyl]-2-pyridyl]methyl]-8-fluoro-quinazoline-4-carboxamide
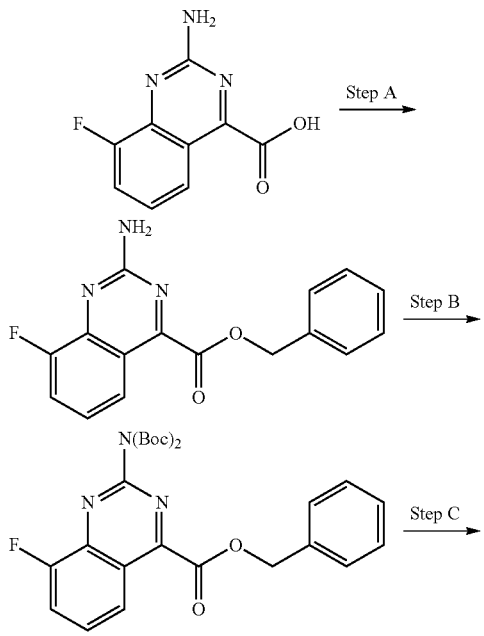
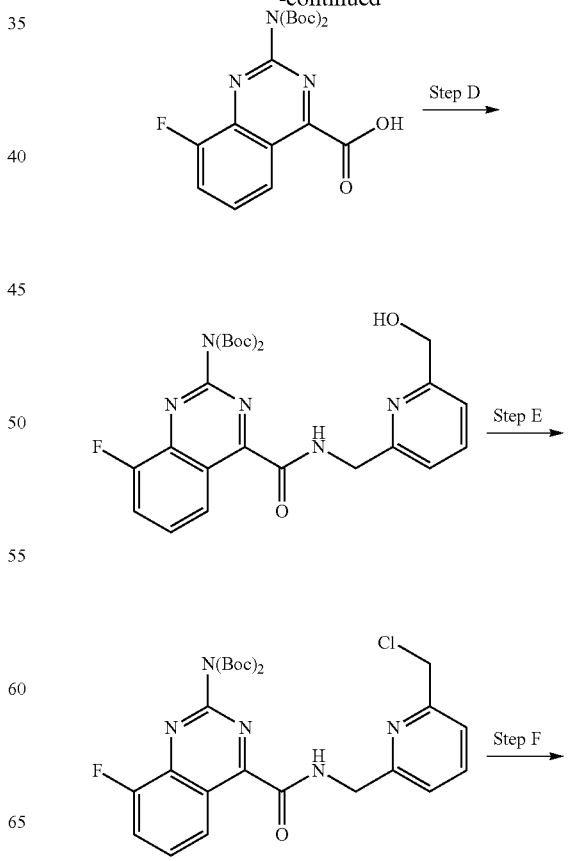

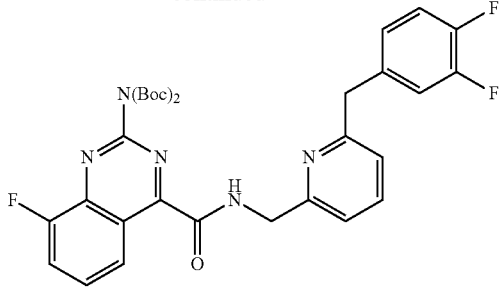

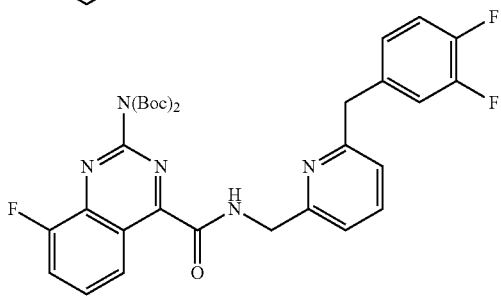

Step A: Benzyl 2-amino-8-fluoro-quinazoline-4-carboxylate

To a solution of 2-amino-8-fluoro-quinazoline-4-carboxylic acid (50 mg, 0.2 mmol) in DMF (6 mL), was added potassium carbonate (50 mg, 0.36 mmol) followed by benzyl bromide (50 mg, 0.3 mmol). The reaction was stirred at room temperature overnight. The reaction mixture was diluted with ethyl acetate (30 mL), and washed water (2×30 mL). The organic phase was concentrated in vacuo and purified by prep-TLC (0-20% MeOH/DCM) to give the title compound.

Step B: Benzyl 2-[bis(tert-butoxycarbonyl)amino]-8-fluoro-quinazoline-4-carboxylate To a solution of Benzyl 2-amino-8-fluoro-quinazoline-4-carboxylate (3 g, 10 mmol) in DMF (60 mL), was added di-tert-butyl dicarbonate (7.7 g, 36 mmol) and N,N-dimethylpyridin-4-amine (3.7 g, 30 mmol). The reaction was stirred at room temperature for 3 h. The reaction mixture was diluted with EtOAc/hexanes (60%, 100 mL), and washed with water (100 mL×2). The organic phase was concentrated in vacuo and purified by prep-TLC on silica (0-100% EtOAc/hexanes) to give the title compound.

Step C: 2-[bis(tert-butoxycarbonyl)amino]-8-fluoro-quinazoline-4-carboxylic acid To a solution of Benzyl 2-[bis(tert-butoxycarbonyl)amino]-8-fluoro-quinazoline-4-carboxylate (4 g, 8 mmol) in MeOH (50 mL) and THF (30 mL) was added sodium hydroxide (2M in water, 6 ml, 12 mmol). The reaction was stirred at room temperature for 45 min. The reaction mixture was diluted with DCM (100 mL). The organic was washed with HCl (0.1 N), dried over sodium sulfate, filtered, and concentrated in vacuo. The residue was suspended in hexane (50 mL) and stirred for 20 min. The solid precipitate was collected by filtration to give the title compound. 1H NMR (400 MHz, CHCl3-d): δ 1.43 (s, 18 H), 7.60-7.80 (m, 2 H), 9.05-9.10 (m, 1 H).

Step D: tert-butyl N-tert-butoxycarbonyl-N-[8-fluoro-4-[[6-(hydroxymethyl)-2-pyridyl]methylcarbamoyl]quinazolin-2-yl]carbamate To a solution of (6-(aminomethyl)pyridin-2-yl)methanol (0.4 g, 2.9 mmol) and 2-[bis(tert-butoxycarbonyl)amino]-8-fluoro-quinazoline-4-carboxylic acid (1.3 g, 3.2 mmol) in THF (30 mL) was added N-ethyl-N-isopropylpropan-2-amine (1.5 g, 12 mmol) and propylphosphonic anhydride solution (50%, 2.7 g, 4.3 mmol). The reaction mixture was stirred at room temperature for 2 h. The reaction mixture was concentrated. The residue was purified by column chromatography on silica (0-100% EtOAc/hexane) to give the title compound as a mixture with tert-butyl (8-fluoro-4-(((6-(hydroxymethyl)pyridin-2-yl)methyl)carbamoyl)quinazolin-2-yl)carbamate which was used in the next step without further purification.

Step E: tert-butyl N-tert-butoxycarbonyl-N-[4-[[6-(chloromethyl)-2-pyridyl]methylcarbamoyl]-8-fluoro-quinazolin-2-yl]carbamate A solution of tert-butyl N-tert-butoxycarbonyl-N-[8-fluoro-4-[[6-(hydroxymethyl)-2-pyridyl]methylcarbamoyl]quinazolin-2-yl]carbamate (0.2 g, 0.4 mmol) in THF (5 mL) was added triethylamine (80 mg, 0.76 mmol) and methanesulfonyl chloride (65 mg, 0.6 mmol). The mixture was stirred at room temperature for 15 min. The reaction mixture was diluted with water (50 mL) and ethylacetate (50 mL). The organic was separated and concentrated in vacuo. The mesylate intermediate was dissolved in acetone (10 mL) and LiCl (50 mg, 1.1 mmol) was added to it. The reaction mixture was stirred at 60° C. for 1 h. The reaction mixture was concentrated in vacuo and then purified by prep-TLC on silica (40% EtOAc/hexane) to give the titled compound.

Step F: 2-amino-N-[[6-[(3,4-difluorophenyl)methyl]-2-pyridyl]methyl]-8-fluoro-quinazoline-4-carboxamide To a mixture of tert-butyl N-tert-butoxycarbonyl-N-[4-[[6-(chloromethyl)-2-pyridyl]methylcarbamoyl]-8-fluoro-quinazolin-2-yl]carbamate (15 mg, 0.03 mmol), (3,4-difluorophenyl)boronic acid (9 mg, 0.06 mmol) in acetonitrile (1 mL) and water (0.2 mL) was added [1,1'-Bis(diphenylphosphino)ferrocene]dichloropalladium(II), complex with dichloromethane (2 mg, 3 μmol) and cesium carbonate (10 mg, 0.06 mmol). The mixture was degassed and refilled with nitrogen. The reaction mixture was heated to 120° C. for 1 h in a microwave reactor. The reaction was concentrated in vacuo and then purified by prep-TLC on silica (70% EtOAc/hexane). The resulting residue was then dissolved with DCM (0.5 mL) and TFA (0.5 mL) was added to it. The mixture was stirred at room temperature for 30 min. The reaction was concentrated and the residue was purified by prep-TLC on silica (8% 7 N ammonia in MeOH/DCM) to give the title compound. LC/MS=424 [M+1]. 1H NMR (DMSO-d): δ 8.41 (d, 2 H); 7.70 (t, 1 H); 7.40-7.50 (m, 1 H); 7.31 (d, 1 H); 7.00-7.25 (m, 5 H); 4.70 (s, 2 H); 4.10 (s, 2 H).

The following examples can be made by applying the strategy described in the Scheme D making the appropriate substitutions. Racemic mixtures were separated by chiral chromatography.

Table IV

The following examples 103-112 were prepared according to the general procedure provided to synthesize example 102, substituting the appropriate quinazoline carboxylic acid for 2-amino-8-fluoro-quinazoline-4-carboxylic acid and substituting the appropriate boronic acid for (3,4-difluorophenyl)boronic acid and the appropriate amine for (6-(aminomethyl)pyridin-2-yl)methanol. The starting materials are commercially available, described above, or may be prepared from commercially available reagents using conventional reactions well known in the art.

TABLE IV

| Ex. | Structure | Name | LC/MS [M + 1] | A2a Ki (nM) |
|---|---|---|---|---|
| 102 | 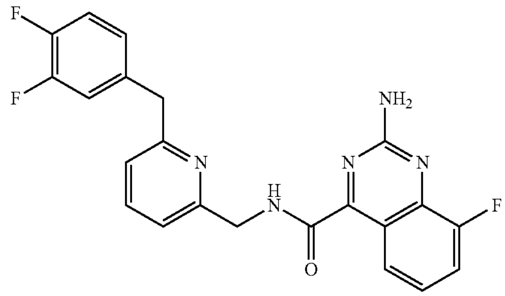 [SMILES: Nc1nc(C(=O)NCc2cccc(Cc3ccc(F)c(F)c3)n2)c2cccc(F)c2n1] | 2-amino-N-[[6-[(3,4-difluorophenyl)methyl]-2-pyridyl]methyl]-8-fluoro-quinazoline-4-carboxamide | 424 | 1.2 |
| 103 | 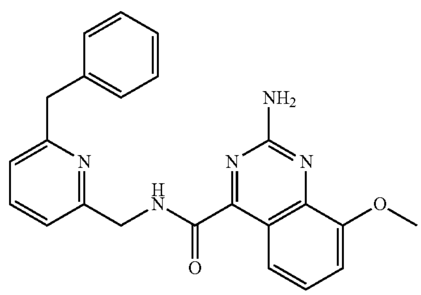 [SMILES: COc1cccc2c(C(=O)NCc3cccc(Cc4ccccc4)n3)nc(N)nc12] | 2-amino-N-((6-benzylpyridin-2-yl)methyl)-8-methoxyquinazoline-4-carboxamide | 400 | 2.5* |
| 104 | 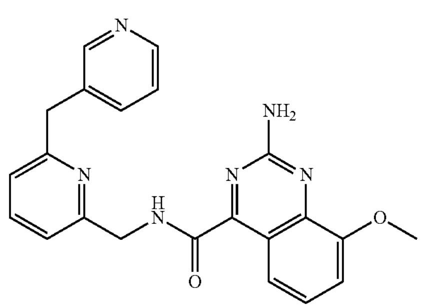 [SMILES: COc1cccc2c(C(=O)NCc3cccc(Cc4cccnc4)n3)nc(N)nc12] | 2-amino-8-methoxy-N-((6-(pyridin-3-ylmethyl)pyridin-2-yl)methyl)quinazoline-4-carboxamide | 401 | 5.0* |
| 105 | 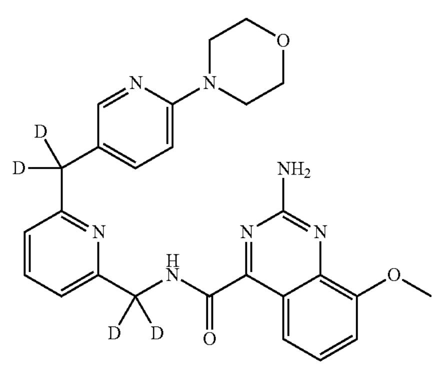 [SMILES: [2H]C([2H])(NC(=O)c1nc(N)nc2c(OC)cccc12)c1cccc(C([2H])([2H])c2ccc(N3CCOCC3)nc2)n1] | 2-amino-N-[dideuterio-[6-[dideuterio-(6-morpholino-3-pyridyl)methyl]-2-pyridyl]methyl]-8-fluoro-quinazoline-4-carboxamide | 490 | 1.6* |

TABLE IV-continued

| Ex. | Structure | Name | LC/MS [M + 1] | A2a Ki (nM) |
|---|---|---|---|---|
| 106 | 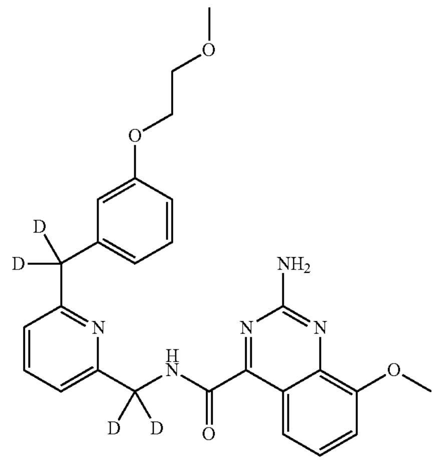 [SMILES: [2H]C([2H])(NC(=O)c1nc(N)nc2c(OC)cccc12)c1cccc(C([2H])([2H])c2cccc(OCCOC)c2)n1] | 2-amino-N-[dideuterio-[6-[dideuterio-[3-(2-methoxyethoxy)phenyl]methyl]-2-pyridyl]methyl]-8-methoxy-quinazoline-4-carboxamide | 478 | 1.9* |
| 107 | 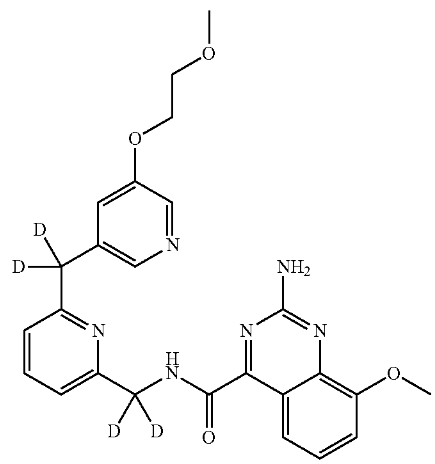 [SMILES: [2H]C([2H])(NC(=O)c1nc(N)nc2c(OC)cccc12)c1cccc(C([2H])([2H])c2cncc(OCCOC)c2)n1] | 2-amino-N-[dideuterio-[6-[dideuterio-[5-(2-methoxyethoxy)-3-pyridyl]methyl]-2-pyridyl]methyl]-8-methoxy-quinazoline-4-carboxamide | 479 | 2.0 |
| 108 | 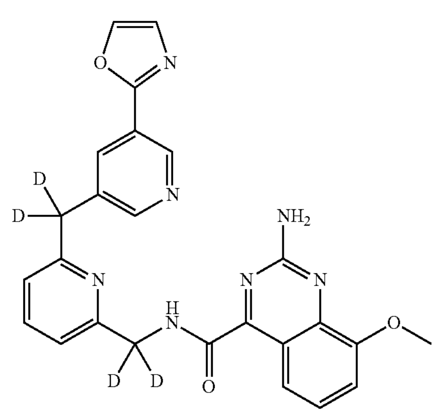 [SMILES: [2H]C([2H])(NC(=O)c1nc(N)nc2c(OC)cccc12)c1cccc(C([2H])([2H])c2cncc(-c3ncco3)c2)n1] | 2-amino-N-[dideuterio-[6-[dideuterio-(5-oxazol-2-yl-3-pyridyl)methyl]-2-pyridyl]methyl]-8-methoxy-quinazoline-4-carboxamide | 472 | 2.1* |

TABLE IV-continued

| Ex. | Structure | Name | LC/MS [M + 1] | A2a Ki (nM) |
|---|---|---|---|---|
| 109 | 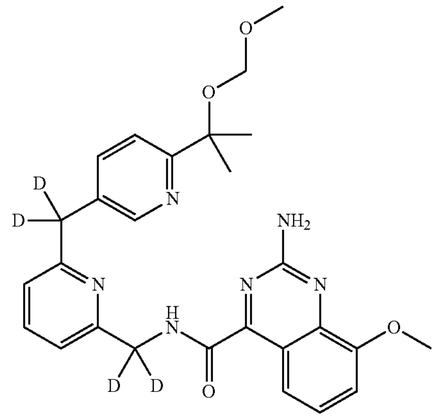 [SMILES: [2H]C([2H])(NC(=O)c1nc(N)nc2c(OC)cccc12)c1cccc(C([2H])([2H])c2ccc(C(C)(C)OCOC)nc2)n1] | 2-amino-N-[dideuterio-[6-[dideuterio-[6-[1-(methoxymethoxy)-1-methyl-ethyl]-3-pyridyl]methyl]-2-pyridyl]methyl]-8-methoxy-quinazoline-4-carboxamide | 507 | 2.3* |
| 110 | 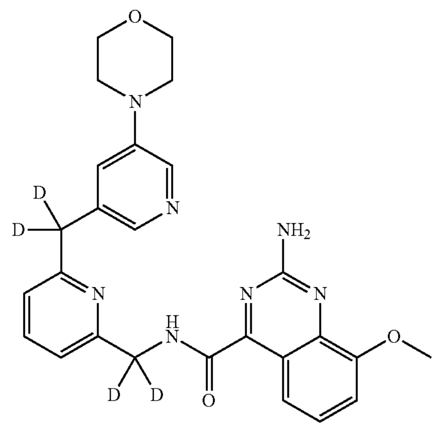 [SMILES: [2H]C([2H])(NC(=O)c1nc(N)nc2c(OC)cccc12)c1cccc(C([2H])([2H])c2cncc(N3CCOCC3)c2)n1] | 2-amino-N-[dideuterio-[6-[dideuterio-(5-morpholino-3-pyridyl)methyl]-2-pyridyl]methyl]-8-methoxy-quinazoline-4-carboxamide | 490 | 2.5* |
| 111 | 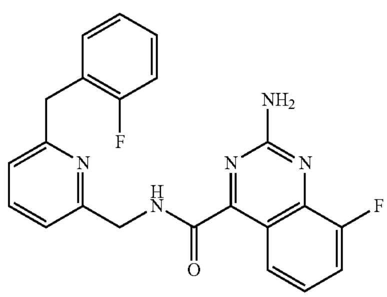 [SMILES: Nc1nc(C(=O)NCc2cccc(Cc3ccccc3F)n2)c2cccc(F)c2n1] | 2-amino-8-fluoro-N-[[6-[(2-fluorophenyl)methyl]-2-pyridyl]methyl]quinazoline-4-carboxamide | 406 | 1.3* |
| 112 | 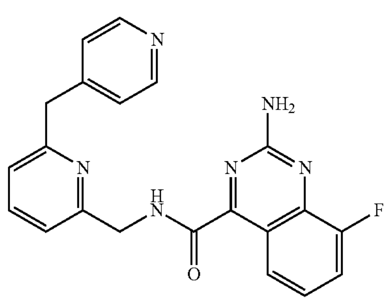 [SMILES: Nc1nc(C(=O)NCc2cccc(Cc3ccncc3)n2)c2cccc(F)c2n1] | 2-amino-8-fluoro-N-[[6-(4-pyridylmethyl)-2-pyridyl]methyl]quinazoline-4-carboxamide | 389 | 1.6 |

Where * appears in the tables it means the assay was run with 1 μg of membranes versus 0.25 μg.

A2a Activity of Compounds of the Invention

Binding affinities of compounds of the invention for the human A2a receptor were determined in a competition binding assay using Scintillation Proximity technology. Thus, 1* μg, or preferably 0.25 μg of membranes from HEK293 cells expressing the human A2a receptor were incubated with a compound of the invention at concentrations ranging from 3000 nM to 0.15 nM in a reaction mixture containing also 0.5 nM of a tritiated form of 5-amino-7-[2-phenethyl]-2-(furan-2-yl)-7H-pyrazolo[4,3-e][1,2,4]triazolo[1,5-c]pyrimidine (the tritiated compound) and 25 μg of wheat germ agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined using the Cheng-Prusoff equation.

Summary of Materials and Methods Used in A2a Activity Determination:

Materials

HEK293 cells expressing the human, rat, dog or monkey adenosine 2a receptor (Purchased from Perkin-Elmer # RBHA2AM400UA).

The Tritiated compound was prepared in-house by MRL Radiochemistry according to published methods.

Wheat germ agglutinin-coated yttrium silicate SPA beads (GE Healthcare #RPNQ0023). Dilute to 25 mg/ml in assay buffer.

Assay Buffer was prepared in house: Dulbecco's calcium and magnesium free phosphate buffered saline+10 mM $MgCl_2$ Adenosine deaminase from calf intestine, 10 mg/2 ml (Roche #10 102 105 001).

DMSO

A2a antagonist standard (9-chloro-1-(2-furanyl)-[1,2,4]triazolo1,5-c]quinazolin-5-amine from Tocris Bioscience)

Compound Dilution

Make eight 1:3 serial dilutions in 100% DMSO from a 3 mM compound stock

Transfer 50 nl of compound into a 384-well OptiPlate (Perkin Elmer).

Typically, final concentrations of compound used in the assay ranged from 3000 nM to 0.152 nM.

Radioisotope

Dilute a solution of the Tritiated compound to 1.25 nM in assay buffer. This is a 2.5× solution. The final concentration in the assay is 0.5 nM. Calculate the concentration by counting two 5 μl aliquots.

Membrane Preparation

Use *1 ug or preferrably 0.25 ug of membrane/well. Dilute membranes to 9.7 μg/ml in assay buffer. Treat with 20 ug/ml adenosine deaminase (ADA) for 15 minutes at room temperature to degrade endogenous adenosine.

Membrane-Bead Mixture

Use 25 μg/well wheat germ agglutinin-coated yttrium silicate SPA beads.

Mix ADA-treated membranes and SPA beads together for 30 min prior to assay.

Assay Assembly

To the Perkin-Elmer Optiplate-384 containing the compound titration add 20 μl of 2.5× solution of the Tritiated compound and 30 μl of the membrane-bead mixture. Incubate for one hour at room temperature with agitation.

Include total binding (assay buffer+1% DMSO) and non-specific binding (CGS15943, 1 μM) wells.

Counting

Allow the beads to settle for one hour.

Count in TopCount.

Calculations

A curve fitting program (i.e., Prism, Activity Base, Chemcart) is used to determine the EC50. The Ki value is calculated using the Cheng-Prusoff equation.

$$Ki = EC50/(1+(\text{radioligand concentration}/Kd))$$

Using the foregoing assay method, the Ki results were obtained using the compounds of the invention described in Tables IIIa, IIIb, and IV. Each example compound tested is reported in the following format: Example number: A2a Ki reported in nM. Thus, for example, the compound Ex-1 was determined to have an Ki using the above-described assay and calculations, of 10.0 nM.

A1 Binding of Compounds of the Invention

Binding affinities of compounds of the invention for the human A1 receptor were determined in a competition binding assay using Scintillation Proximity technology. Thus, 5 of membranes from CHO-K1 cells expressing the human A1 receptor were incubated with a compound of the invention at concentrations ranging from 3000 nM to 0.15 nM in a reaction mixture containing also 0.7 nM of a tritiated form of 8-Cyclopentyl-1,3-dipropylxanthine (the tritiated compound) and 25 μg of wheat germ agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined in a similar fashion described with A2a binding.

Summary of Materials and Methods Used in A1 Binding Determination:

Cells expressing the human, rat, dog or monkey adenosine 1 receptor (Purchased from Perkin-Elmer # ES-010-M400UA

[$^3$H]DPCPX (purchased from Perkin-Elmer NET-974, 8-cyclopentyl-1,3-dipropylxanthine, [dipropyl-2,3-$^3$H(N)].

Wheatgerm agglutinin-coated yttrium silicate SPA beads (Purchased from GE Healthcare #RPNQ0023). Dilute to 25 mg/ml in assay buffer. Store at 4° C.

Assay Buffer—Dulbecco's phosphate buffered saline without calcium and without magnesium+10 mM $MgCl_2$ Adenosine deaminase from calf intestine, 10 mg/2 ml (Roche #10 102 105 001).

DMSO

DPCPX (A1 antagonist) from Tocris Bioscience

Compound Dilution

Dilute compounds to 1 mM in 100% DMSO

Make serial dilutions as necessary (i.e., 1:10, 1:3) in 100% DMSO.

Dilute 1:20 into assay buffer (i.e. 3 ul into 57 ul buffer). This is a 5× solution in 5% DMSO.

Radioisotope

Dilute [$^3$H]DPCPX to 1.75 nM in assay buffer. This is a 2.5× solution. The final concentration in the assay is 0.7 nM. Calculate the concentration by counting two 5 ul aliquots.

Membrane Preparation

Use 5 ug of membrane/well. Dilute membranes to 250 ug/ml in assay buffer. Treat with 20 ug/ml adenosine deaminase (ADA) for 15 minutes at room temperature to degrade endogenous adenosine.

Membrane-Bead Mixture

Use 25 ug/well wheatgerm agglutinin-coated yttrium silicate SPA beads

Mix ADA-treated membranes and SPA beads together for 30 min prior to assay.

Assay Assembly

Add in order to a Perkin-Elmer Optiplate-384: 10 ul of 5× compound, 20 ul of 2.5× [$^3$H]DPCPX, 20 ul membrane-bead mixture. Incubate for one hour at room temperature with agitation.

Include total binding (assay buffer+1% DMSO) and non-specific binding (DPCPX, 1 uM) wells.

Counting and Calculations

Counting and calculations were performed as described within the "A2a Activity Binding of Compounds of the Invention" section. Selectivity was calculated by dividing the A1 binding Ki by the A2a binding Ki. Using the foregoing methods, the following results were obtained using compounds of the invention described herein. Each example compound tested is reported in the following format: Example number: A2a selectivity. Thus, for example, the compound Example 1 was determined to have an A2a A1 binding selectivity using the above-described methods, and is accordingly reported as "Ex-1: 145": Ex-1:=145; Ex-2:=193; Ex-3:=600; Ex-4:=314; Ex-5:=146; Ex-6:=102; Ex-7:=169; Ex-8:=4; Ex-9:=764; Ex-10:=113; Ex-11:=208; Ex-12:=32; Ex-13:=112; Ex-14:=273; Ex-15:=319; Ex-16:=114; Ex-17:=184; Ex-18:=412; Ex-19:=53; Ex-20:=89; Ex-21:=82; Ex-22:=52; Ex-23:=110; Ex-24:=180; Ex-25:=221; Ex-26:=89; Ex-27:=148; Ex-28:=117; Ex-29:=118; Ex-30:=138; Ex-31:=105; Ex-32:=370; Ex-33:=60; Ex-34:=46; Ex-35:=48; Ex-36:=114; Ex-37:=32; Ex-38:=94; Ex-39:=9; Ex-40:=3; Ex-41:=56; Ex-42:=39; Ex-43:=84; Ex-44:=531; Ex-45:=230; Ex-46:=484; Ex-47:=36; Ex-48:=447; Ex-49:=251; Ex-50:=160; Ex-51:=90; Ex-52:=140; Ex-53:=63; Ex-54:=49; Ex-55:=36; Ex-56:=111; Ex-57:=67; Ex-58: =16; Ex-59:=32; Ex-60:=67; Ex-61:=100; Ex-62:=297; Ex-63:=59; Ex-64:=235; Ex-65:=50; Ex-66:=3; Ex-67:=297; Ex-68:=44; Ex-69:=63; Ex-70:=19; Ex-71:=60; Ex-72: =30; Ex-73:=33; Ex-74:=18; Ex-75:=14; Ex-76:=115; Ex-77:=62; Ex-78:=75; Ex-79:=14; Ex-80:=21; Ex-81:=12; Ex-82:=56; Ex-83:=3; Ex-84:=25; Ex-85:=4; Ex-86:=141; Ex-87:=3; Ex-88:=8; Ex-89:=13; Ex-91:=70; Ex-92:=560; Ex-93:=55; Ex-94:=11; Ex-95:=55; Ex-96: =12; Ex-97:=1; Ex-98:=133; Ex-99:=8; Ex-100:=163; Ex-101:=88; Ex-102:=33; Ex-103:=42; Ex-104:=93; Ex-105:=117; Ex-106:=70; Ex-107:=95; Ex-108:=77; Ex-109:=120; Ex-110:=64; Ex-111:=28; Ex-112:=31

The invention claimed is:

1. A compound of structural formula I:

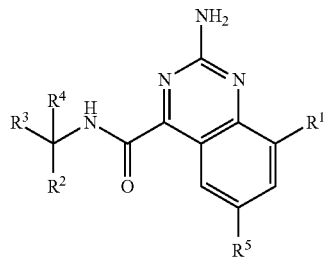

I or a pharmaceutically acceptable salt thereof, wherein:
R represents hydrogen or —$C_{1-6}$alkyl;
$R^1$ is selected from the group consisting of —$C_{1-6}$alkyl, —$OC_{1-6}$alkyl, halogen, —$C_{1-4}$ haloalkyl, —$OC_{1-4}$haloalkyl, CN, —$SC_{1-6}$alkyl, —$SO_2C_{1-6}$alkyl, and —$(CH_2)_nC_{4-10}$ heteroaryl;
$R^2$ and $R^3$ when present are independently selected from the group consisting of hydrogen, deuterium, $C_{3-10}$cycloalkyl, and $C_{1-6}$ alkyl, said alkyl optionally substituted with 1 to 3 groups of $R^b$; or $R^2$ and $R^3$ can combine to form a 3 to 6 membered cycloalkyl ring;
$R^4$ when present represents —$(CH_2)_nC_{6-10}$ aryl, or —$(CH_2)_nC_{4-10}$ heterocycle, said aryl and heterocycle optionally substituted with 1 to 3 groups of $R^a$; or
$R^2$, $R^3$ and $R^4$ can combine to form a $C_{4-10}$ heterocyclic group, said heterocyclic group optionally substituted with 1 to 3 groups of $R^a$; or
R5 represents hydrogen or halogen;
$R^a$ is selected from the group consisting of —CN, halogen, —$C_{1-4}$haloalkyl, —$OC_{1-4}$haloalkyl, —$C_{1-6}$alkyl, —$(CH_2)_nOR$, —$(CH_2)_nC_{6-10}$aryl, —$(CH_2)_nC_{4-10}$heterocycle,
—$(CH_2)_nO(CH_2)_n$ $C_{3-6}$cycloalkyl, $C_{3-6}$cycloalkyl, $C(C_{3-6}$cycloalkyl)OR, —$(CH_2)_nO(CH_2)_nC_{6-10}$ aryl, —$(CH_2)_nO(CH_2)_nC_{4-10}$ heterocycle, —$(CH_2)_nSC_{6-10}$ aryl, —$(CH_2)_nSC_{4-10}$ heterocycle, =O, C(O)OR, said alkyl, cycloalkyl, aryl and heterocycle, wherein one or more hydrogen atoms therein are optionally replaced by an equal number of deuterium atoms, and optionally substituted with 1 to 3 groups of $R^b$;
$R^b$ is selected from the group consisting of —$C_{1-6}$alkyl, —$C_{1-6}$alkylOR, OR, $O(CH_2)_{1-2}OR$, —$C_{1-4}$haloalkyl, halogen, CN, —$C_{6-10}$ aryl, —$C_{4-10}$ heterocycle, $C(CH_3)_2O(CH_2)_{1-2}OR$, said alkyl, aryl and heterocycle optionally substituted with 1 to 3 groups of $R^c$;
$R^c$ is selected from the group consisting of: (i) —$C_{1-6}$alkyl; (ii) halogen; (iii) —$C_{1-6}$alkylOR; (iv) $O(CH_2)_{1-2}OR$; and (v) OR; and
n represents 0-4.

2. The compound according to claim 1 wherein $R^1$ is selected from the group consisting of —$OC_{1-6}$alkyl, —$C_{1-4}$haloalkyl, —$OC_{1-4}$haloalkyl, and halogen, or a pharmaceutically acceptable salt thereof.

3. The compound according to claim 1 wherein $R^1$ is —$OCH_3$, or a pharmaceutically acceptable salt thereof.

4. The compound according to claim 1, or a pharmaceutically acceptable salt thereof, wherein both of $R^2$ and $R^3$ are hydrogen or deuterium.

5. The compound according to claim 1, or a pharmaceutically acceptable salt thereof wherein $R^4$ is —$(CH_2)_nC_{6-10}$ aryl optionally substituted with 1 to 3 groups of $R^a$.

6. The compound according to claim 5 wherein the $R^4$ is aryl which is optionally substituted phenyl.

7. The compound according to claim 1, or a pharmaceutically acceptable salt thereof, wherein $R^4$ is —$(CH_2)_nC_{4-10}$ heterocycle and is optionally substituted with 1 to 3 groups of $R^a$, wherein, optionally, one or more hydrogen atoms in $R^a$ is substituted by deuterium.

8. The compound according to claim 7 wherein the heterocycle is selected from the group consisting unsubstituted or substituted pyridyl, quinolyl, pyridinone, oxazolyl, pyrimidinyl, benzodioxolyl, imidazopyridyl, thiazolyl, isoxazolyl, dihydrobenzoxazinyl and piperidyl, or a pharmaceutically acceptable salt thereof.

9. The compound according to claim 8 wherein the heterocycle is selected from the group consisting substituted pyridyl, quinolyl, and pyridinone, or a pharmaceutically acceptable salt thereof.

10. The compound according to claim 1, or a pharmaceutically acceptable salt thereof, wherein $R^2$, $R^3$ and $R^4$ combine to form a $C_{4-10}$ heterocyclic group selected from the group consisting of indanyl, tetralinyl, dihydrocyclopentapyridinyl, and tetrahydroquinolinyl, said groups optionally substituted with 1 to 3 groups of $R^a$.

11. The compound according to claim 1 or a pharmaceutically acceptable salt thereof, wherein $R^a$ is selected from the group consisting of halogen, —$C_{1-4}$haloalkyl, —$C_{1-6}$alkyl, —$(CH_2)_nOR$, —$(CH_2)_nC_{6-10}$ aryl, —$(CH_2)_nC_{4-10}$ heterocycle, —$(CH_2)O(CH_2)_nC_{6-10}$ aryl, —$(CH_2)O(CH_2)_nC_{4-10}$ heterocycle, $C_{3-6}$cycloalkyl, —O—$CH_3$, —C(O)OR, $C(D_2)C_{6-10}$ aryl, —$C(D_2)C_{4-10}$ heterocycle, said alkyl, aryl and heterocycle optionally substituted with 1 to 3 groups of $R^b$.

12. The compound according to claim 1, represented by structural formula II:

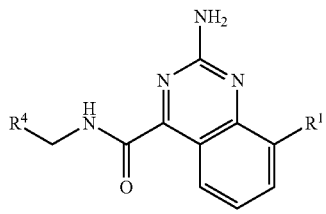

II or a pharmaceutically acceptable salt thereof.

13. The compound according to claim 12 wherein $R^4$ is selected from the group consisting of phenyl, pyridyl, pyridinone, quinolyl, oxazolyl, pyrimidinyl, benzodioxolyl, imidazopyridinyl, thiazolyl, isoxazolyl, dihydrobenzoxazinyl, and piperidyl, said groups optionally substituted with 1 to 3 groups of $R^a$, and $R^1$ is selected from the group consisting of —$OC_{1-6}$alkyl, —$C_{1-4}$ haloalkyl, —$OC_{1-4}$haloalkyl, and halogen, or a pharmaceutically acceptable salt thereof.

14. The compound according to claim 13 wherein $R^a$ is selected from the group consisting of —$C(CH_3)_2OH$, $OCH_3$, $CF_3$, —$OCH(CH_3)_2$, methyl, ethyl, propyl, butyl, —CH$(CH_3)_2$, —$C(CH_3)(CF_3)$—OH, $CH_2OCH_2CH(CH_3)_2$, a moiety of the formula:

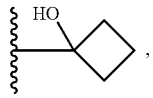

—$CH_2OH$, fluorine, chlorine, bromine, iodine, cyclobutyl, cyclopropyl, $(CH_2)_n$phenyl, $(CH_2)_n$pyridyl, $(CH_2)_n$piperidyl, $(CH_2)_n$piperizinyl, oxo, $(CH_2)_n$pyrazolyl, $(CH_2)_n$pyrimidinyl, $(CH_2)_n$thiazolyl, $(CH_2)_n$oxazolyl, $C(O)OCH_3$, $(CH_2)_n$morpholinyl, $(CH_2)_n$—O—phenyl, $(CH_2)_n$—S—phenyl, $(CH_2)_n$—O—pyridyl, $(CH_2)_n$—S—pyridyl, $(CH_2)_n$—S—benzimidazolyl, $CH_2$—O—$CH_2$-cyclopentyl, $(CH_2)_n$—O—tetrahydrofuranyl, $(CD_2)_n$phenyl, and $(CD_2)_n$pyridyl, said methyl, ethyl, propyl, butyl, phenyl, pyridyl, piperidyl, piperizinyl, pyrazolyl, pyrimidinyl, thiazolyl, oxazolyl, morpholinyl, and benzimidazolyl optionally substituted with 1 to 3 groups of $R^b$, or a pharmaceutically acceptable salt thereof.

15. The compound according to any of claims 12-14 wherein $R^4$ is unsubstituted or substituted pyridyl or pyridinone, or a pharmaceutically acceptable salt thereof.

16. The compound according any of claims 12-14 wherein $R^4$ is unsubstituted or substituted quinolyl, or a pharmaceutically acceptable salt thereof.

17. A compound which is:
2-amino-N-[[6-(1-hydroxy-1-methyl-ethyl)-3-methoxy-2-pyridyl]methyl]-8-methoxy-quinazoline-4-carboxamide,
2-amino-N-[[6-(1-hydroxy-1-methyl-ethyl)-3-methyl-2-pyridyl]methyl]-8-methoxy-quinazoline-4-carboxamide,
2-amino-8-methoxy-N-[[6-(2,2,2-trifluoro-1-hydroxy-1-methyl-ethyl)-2-pyridyl]methyl]quinazoline-4-carboxamide,
2-amino-N-[[6-(1-hydroxycyclobutyl)-2-pyridyl]methyl]-8-methoxy-quinazoline-4-carboxamide,
2-amino-N-[(6-isopropyl-2-pyridyl)methyl]-8-methoxy-quinazoline-4-carboxamide,
2-amino-N-[(6-cyclobutyl-2-pyridyl)methyl]-8-methoxy-quinazoline-4-carboxamide,
2-amino-N-[(6-cyclopropyl-2-pyridyl)methyl]-8-methoxy-quinazoline-4-carboxamide,
2-amino-N-[[6-(3-hydroxyphenyl)-2-pyridyl]methyl]-8-methoxy-quinazoline-4-carboxamide,
2-amino-N-[[6-(1-hydroxy-1-methyl-ethyl)-2-pyridyl]methyl]-8-methoxy-quinazoline-4-carboxamide,
2-amino-8-methoxy-N-[[6-(2-pyridyl)-2-pyridyl]methyl]quinazoline-4-carboxamide,
2-amino-N-[(3,6-dimethyl-2-pyridyl)methyl]-8-methoxy-quinazoline-4-carboxamide,
2-amino-8-methoxy-N-(8-quinolylmethyl)quinazoline-4-carboxamide,
2-amino-N-[(1-ethyl-2-oxo-3-pyridyl)methyl]-8-methoxy-quinazoline-4-carboxamide,
2-amino-8-methoxy-N-[(6-methyl-2-pyridyl)methyl]quinazoline-4-carboxamide,
2-amino-N-(8-isoquinolylmethyl)-8-methoxy-quinazoline-4-carboxamide,
2-amino-8-methoxy-N-(m-tolylmethyl)quinazoline-4-carboxamide,
2-amino-8-methoxy-N-[[6-(trifluoromethyl)-2-pyridyl]methyl]quinazoline-4-carboxamide,
2-amino-8-methoxy-N-[[3-(trifluoromethyl)-2-pyridyl]methyl]quinazoline-4-carboxamide,
2-amino-N-[(3-fluoro-6-methyl-2-pyridyl)methyl]-8-methoxy-quinazoline-4-carboxamide,
2-amino-8-methoxy-N-[(6-methoxy-2-pyridyl)methyl]quinazoline-4-carboxamide,
2-amino-8-methoxy-N-[(5-methoxy-2-pyridyl)methyl]quinazoline-4-carboxamide,
2-amino-8-methoxy-N-[(3-methoxy-2-pyridyl)methyl]quinazoline-4-carboxamide,
2-amino-8-methoxy-N-[(3-methyl-2-pyridyl)methyl]quinazoline-4-carboxamide,
2-amino-N-[(3-fluoro-2-pyridyl)methyl]-8-methoxy-quinazoline-4-carboxamide,
2-amino-N-[(5-fluoro-2-pyridyl)methyl]-8-methoxy-quinazoline-4-carboxamide,
2-amino-N-[(6-fluoro-2-pyridyl)methyl]-8-methoxy-quinazoline-4-carboxamide,
2-amino-N-[(3,5-dimethyl-2-pyridyl)methyl]-8-methoxy-quinazoline-4-carboxamide,
2-amino-N-[(3,5-difluoro-2-pyridyl)methyl]-8-methoxy-quinazoline-4-carboxamide,
2-amino-8-methoxy-N-(2-quinolylmethyl)quinazoline-4-carboxamide,
2-amino-8-methoxy-N-[(5-methyl-4-phenyl-oxazol-2-yl)methyl]quinazoline-4-carboxamide,
2-amino-N-(6,7-dihydro-5H-cyclopenta[b]pyridin-7-yl)-8-methoxy-quinazoline-4-carboxamide,
2-amino-N-[(1R)-indan-1-yl]-8-methoxy-quinazoline-4-carboxamide,
2-amino-8-methoxy-N-[(2R)-tetralin-2-yl]quinazoline-4-carboxamide, 2-amino-8-methoxy-N-[(8S)-5,6,7,8-tetrahydroquinolin-8-yl]quinazoline-4-carboxamide,
2-amino-N-[(1R)-2-hydroxy-1-phenyl-ethyl]-8-methoxy-quinazoline-4-carboxamide,
2-amino-N-[(1R)-2-hydroxy-1-(2-quinolyl)ethy]-8-methoxy-quinazoline-4-carboxamide,
2-amino-8-methoxy-N-(pyrimidin-2-ylmethyl)quinazoline-4-carboxamide,
2-amino-8-methoxy-N-[1-methyl-1-(2-pyridyl)ethyl]quinazoline-4-carboxamide,
2-amino-8-methoxy-N-[1-(2-pyridyl)cyclopropyl]quinazoline-4-carboxamide,
2-amino-8-methoxy-N-[[2-(3-pyridyl)phenyl]methyl]quinazoline-4-carboxamide,
2-amino-N-[(2,2-difluoro-1,3-benzodioxol-4-yl)methyl]-8-methoxy-quinazoline-4-carboxamide,
2-amino-8-methoxy-N-[[2-(2-pyridyl)phenyl]methyl]quinazoline-4-carboxamide,
2-amino-N-[[6-[(2-fluorophenoxy)methyl]-2-pyridyl]methyl]-8-methoxy-quinazoline-4-carboxamide,
2-amino-N-[[6-[(4-fluorophenoxy)methyl]-2-pyridyl]methyl]-8-methoxy-quinazoline-4-carboxamide,
2-amino-8-fluoro-N-[[6-(2-pyridyloxymethyl)-2-pyridyl]methyl]quinazoline-4-carboxamide,
2-amino-N-[[6-[(4-cyanophenoxy)methyl]-2-pyridyl]methyl]-8-fluoro-quinazoline-4-carboxamide,
2-amino-N[[6-(cyclopentoxymethyl)-2-pyridyl]methyl]-8-methoxy-quinazoline-4-carboxamide,
2-amino-N[[6-(cyclopentylmethoxymethyl)-2-pyridyl]methyl]-8-methoxy-quinazoline-4-carboxamide,
2-amino-N[[6-(cyclopropylmethoxymethyl)-2-pyridyl]methyl]-8-methoxy-quinazoline-4-carboxamide,
2-amino-N[[6-(isobutoxymethyl)-2-pyridyl]methyl]-8-methoxy-quinazoline-4-carboxamide,
2-amino-8-methoxy-N-[[6-[[(3S)-tetrahydrofuran-3-yl]oxymethyl]2-pyridyl]methyl]quinazoline-4-carboxamide,
2-amino-8-methoxy-N-[[3-(morpholinomethyl)phenyl]methyl]quinazoline-4-carboxamide,
2-amino-N-[[6-[(3-fluorophenoxy)methyl]-2-pyridyl]methyl]-8-methoxy-quinazoline-4-carboxamide,
2-amino-N-[[6-[(4-fluoropheny)sulfanylmethyl]-2-pyridyl]methyl]-8-methoxy-quinazoline-4-carboxamide,
2-amino-N-[[6-(1H-benzimidazol-2-ylsulfanylmethyl)-2-pyridyl]methyl]-8-methoxy-quinazoline-4-carboxamide,
2-amino-8-fluoro-N-[[6-(hydroxymethyl)-2-pyridyl]methyl]quinazoline-4-carboxamide,
2-amino-N-[dideuterio-[6-[(5-methoxy-3-pyridyl)oxy]-2-pyridyl]methyl]-8-methoxy-quinazoline-4-carboxamide,
2-amino-N-[dideuterio-[6-[4-(2-methoxyethoxy)phenoxyl]-2-pyridyl]methyl]-8-fluoro-quinazoline-4-carboxamide,
2-amino-N-[dideuterio-[6-[4-[4-(2-methoxyethoxy)phenyl]piperazin-1-yl]-2-pyridyl]methyl]-8-methoxy-quinazoline-4-carboxamide,
2-amino-8-methoxy-N-[(1-methyl-2-oxo-3-pyridyl)methyl]quinazoline-4-carboxamide,
2-amino-8-fluoro-N-[(2-pyrazol-1-ylphenyl)methyl]quinazoline-4-carboxamide,
2-amino-8-fluoro-N-[[6-(2-pyridyl)-2-pyridyl]methyl]quinazoline-4-carboxamide,
2-amino-8-fluoro-N-[(2-pyrimidin-2-ylphenyl)methyl]quinazoline-4-carboxamide,
2-amino-8-fluoro-N-[[6-(3-isopropylphenyl)-2-pyridyl]methyl]quinazoline-4-carboxamide,
2-amino-8-fluoro-N-[[6-(3-isopropoxyphenyl)-2-pyridyl]methyl]quinazoline-4-carboxamide,
2-amino-8-fluoro-N-[(3-pyrimidin-2-yl-2-pyridyl)methyl]quinazoline-4-carboxamide,
2-amino-8-fluoro-N-[[3-(5-methyl-2-pyridyl)-2-pyridyl]methyl]quinazoline-4-carboxamide,
2-amino-8-fluoro-N-[[6-(4-methylthiazol-2-yl)-2-pyridyl]methyl]quinazoline-4-carboxamide,
2-amino-8-fluoro-N-[(6-oxazol-5-yl-2-pyridyl)methyl]quinazoline-4-carboxamide,
2-amino-N-[[6-(difluoromethyl)-2-pyridyl]methyl]-8-fluoro-quinazoline-4-carboxamide,
2-amino-8-fluoro-N-[(5-methyl-2-pyridyl)methyl]quinazoline-4-carboxamide,
2-amino-8-fluoro-N-[2-(5-methyl-2-pyridyl)ethyl]quinazoline-4-carboxamide,
methyl 2-[[(2-amino-8-fluoro-quinazoline-4-carbonyl)amino]methyl]benzoate,
methyl 6-[[(2-amino-8-fluoro-quinazoline-4-carbonyl)amino]methyl]pyridine-2-carboxylate,
2-amino-8-fluoro-N-[(3-fluoro-6-methyl-2-pyridyl)methyl]quinazoline-4-carboxamide,
2-amino-8-fluoro-N-[(6-methoxy-3-methyl-2-pyridyl)methyl]quinazoline-4-carboxamide,
2-amino-8-fluoro-N-[(6-isopropoxy-2-pyridyl)methyl]quinazoline-4-carboxamide,
2-amino-8-fluoro-N-[[6-(4-hydroxy-4-methyl-1-piperidyl)-2-pyridyl]methyl]quinazoline-4-carboxamide,
2-amino-8-fluoro-N-(imidazo[1,5-a]pyridin-5-ylmethyl)quinazoline-4-carboxamide,
2-amino-8-fluoro-N-[(8-methylimidazo[1,2-a]pyridin-2-yl)methyl]quinazoline-4-carboxamide,
2-amino-8-fluoro-N-[(2-isopropylthiazol-4-yl)methyl]quinazoline-4-carboxamide,
2-amino-N-[(5-cyclopropylisoxazol-3-yl)methyl]-8-fluoro-quinazoline-4-carboxamide,
2-amino-N-(3,4-dihydro-2H-1,4-benzoxazin-8-ylmethyl)-8-fluoro-quinazoline-4-carboxamide,
N-(1-adamantylmethyl)-2-amino-8-fluoro-quinazoline-4-carboxamide,
2-amino-8-fluoro-N-[[1-(5-fluoropyrimidin-2-yl)-4-piperidyl]methyl]quinazoline-4-carboxamide,
2-amino-8-fluoro-N-(norbornan-2-ylmethyl)quinazoline-4-carboxamide,
2-amino-8-fluoro-N-[(1R)-1-(8-quinolyl)ethyl]quinazoline-4-carboxamide,
2-amino-8-chloro-N-(8-quinolylmethyl)quinazoline-4-carboxamide,
2-amino-N-(8-quinolylmethyl)-8-(trifluoromethyl)quinazoline-4-carboxamide,
2-amino-6,8-dichloro-N-[(6-methyl-2-pyridyl)methyl]quinazoline-4-carboxamide,
2-amino-8-methylsulfanyl-N-(8-quinolylmethyl)quinazoline-4-carboxamide,
2-amino-8-methylsulfonyl-N-(8-quinolylmethyl)quinazoline-4-carboxamide,
2-amino-8-bromo-N-(8-quinolylmethyl)quinazoline-4-carboxamide,
2-amino-8-pyrimidin-5-yl-N-(8-quinolylmethyl)quinazoline-4-carboxamide,
2-amino-N-[(3-fluoro-6-methyl-2-pyridyl)methyl]-8-oxazol-2-yl-quinazoline-4-carboxamide,
2-amino-8-iodo-N-(pyrimidin-2-ylmethyl)quinazoline-4-carboxamide, 2-amino-8-cyano-N-(8-quinolylmethyl)quinazoline-4-carboxamide, 2-amino-N-(8-quinolylmethyl)-8-(trifluoromethoxy)quinazoline-4-carboxamide, 2-amino-N-[[6-[(3,4-difluorophenyl)methyl]-2-pyridyl]methyl]-8-fluoro-quinazoline-4-carboxamide, 2-amino-N-((6-benzylpyridin-2-yl)methyl)-8-methoxy-quinazoline-4-carboxamide, 2-amino-8-methoxy-N-((6-(pyridin-3-ylmethyl)pyridin-2-yl)methyl)quinazoline-4-carboxamide, 2-amino-N-[dideuterio-[6-[dideuterio-(6-morpholino-3-pyridyl)methyl]-2-pyridyl]methyl]-8-fluoro-quinazoline-4-carboxamide, 2-amino-N-[dideuterio[6-[dideuterio-[3-(2-methoxyethoxy)phenyl]methyl]-2-pyridyl]methyl]-8-methoxy-quinazoline-4-carboxamide, 2-amino-N-[dideuterio[6-[dideuterio-[5-(2-methoxyethoxy)-3-pyridyl]methyl]-2-pyridyl]methyl]-8-methoxy-quinazoline-4-carboxamide, 2-amino-N-[dideuterio[6-[dideuterio-(5-oxazol-2-yl-3-pyridyl)methyl]-2-pyridyl]methyl]-8-methoxy-quinazoline-4-carboxamide, 2-amino-N-[dideuterio-[6-[dideuterio-[6-[1-(methoxymethoxy)-1-methyl-ethyl]-3-pyridyl]methyl]-2-pyridyl]methyl]-8-methoxy-quinazoline-4-carboxamide, 2-amino-N-[dideuterio-[6-[dideuterio-(5-morpholino-3-pyridyl)methyl]-2-pyridyl]methyl]-8-methoxy-quinazoline-4-carboxamide, 2-amino-8-fluoro-N-[[6-[(2-fluoropheny)methyl]-2-pyridyl]methyl]quinazoline-4-carboxamide, 2-amino-8-fluoro-N-[[6-(4-pyridylmethyl)-2-pyridyl]methyl]quinazoline-4-carboxamide, or a pharmaceutical salt thereof.

18. A pharmaceutical composition comprising a compound of formula I of claim 1 or a pharmaceutically acceptable salt thereof, and at least one excipient.

\* \* \* \* \*